US007179593B1

(12) United States Patent
Roy et al.

(10) Patent No.: US 7,179,593 B1
(45) Date of Patent: Feb. 20, 2007

(54) ESTROGEN RECEPTOR SITE-SPECIFIC RIBOZYMES AND USES THEREOF FOR ESTROGEN DEPENDENT TUMORS

(75) Inventors: Arun K. Roy, San Antonio, TX (US); Yan Lavrovsky, Geneva (CH); Rakesh K. Tyagi, New Delhi (IN); Chung S. Song, San Antonio, TX (US); Bandana Chatterjee, San Antonio, TX (US); Shuo Chen, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 638 days.

(21) Appl. No.: 10/009,420

(22) PCT Filed: Jun. 2, 2000

(86) PCT No.: PCT/US00/15243

§ 371 (c)(1), (2), (4) Date: Feb. 3, 2003

(87) PCT Pub. No.: WO00/74485

PCT Pub. Date: Dec. 14, 2000

Related U.S. Application Data

(60) Provisional application No. 60/137,470, filed on Jun. 4, 1999.

(51) Int. Cl.

| | |
|---|---|
| ***C12Q 1/68*** | (2006.01) |
| ***C12P 19/34*** | (2006.01) |
| ***C12N 15/88*** | (2006.01) |
| ***C07H 21/02*** | (2006.01) |
| ***C07H 21/04*** | (2006.01) |

(52) U.S. Cl. ...................... 435/6; 435/91.1; 435/91.31; 435/455; 435/458; 536/23.1; 536/24.5

(58) Field of Classification Search .................... 435/6, 435/91.1, 91.31, 455, 458; 536/23.1, 24.5; 514/44

See application file for complete search history.

(56) References Cited

U.S. PATENT DOCUMENTS 5,496,698 A 3/1996 Draper et al. .................. 435/6

(Continued)

FOREIGN PATENT DOCUMENTS

WO WO 99/54459 10/1999

(Continued)

OTHER PUBLICATIONS

Amarzguioui and Prydz, "Hammerhead Ribozyme Design and Application," *CMLS*, 54:1175-1202, 1998.

(Continued)

*Primary Examiner*—Jane Zara
(74) *Attorney, Agent, or Firm*—Fulbright & Jaworski L.L.P.

(57) ABSTRACT

Highly specific hammerhead ribozymes are provided that human target estrogen receptor mRNA. These ribozymes, designated RZ1 through RZ7 provide predictable mRNA cleavage products. Methods for inhibiting estrogen-dependent tumor growth, such as that characteristic of breast cancer, are also provided employing these ribozymes. One or both of the ribozymes may be used together or separately with equal efficiency. The ribozymes possess a sequence region with a catalytic core that provides the attributed catalytic activity to these ribozymes.

28 Claims, 12 Drawing Sheets

RZ-2

RZ-1

U.S. PATENT DOCUMENTS

| | | | |
|---|---|---|---|
| 5,525,468 A | 6/1996 | McSwiggen | 435/6 |
| 5,834,440 A | 11/1998 | Goldenberg et al. | 514/44 |

FOREIGN PATENT DOCUMENTS

| | | |
|---|---|---|
| WO | WO 00/74485 | 12/2000 |

OTHER PUBLICATIONS

Branch, "A Good Antisense Molecule is Hard to Find," *TIBS*, 23:45-50, 1998.

Chen et al., "Catalytic Cleavage of the Androgen Receptor Messenger RNA and Functional Inhibition of Androgen Receptor Activity by a Hammerhead Ribozyme," *Mol. Endocrinol.*, 12(10):1558-1566, 1998.

Chen, "Molecular Strategies for Selective Inhibition of Androgen Receptor Gene Expression," *A Dissertation presented to the Faculty of The University of Texas Graduate School of Biomedical Sciences at San Antonio in partial fulfillment of the requirements for the Degree of Doctor of Philosophy in Cellular and Structural Biology*, Mar. 1997; Also, vol. 58/03-B of Dissertation Abstracts International, p. 1103, 1997.

Chen and Roy, "Specific Inactivation of the Androgen Receptor Messager RNA by a Hammerhead Ribozyme," *Premier Event in 10th International Congress of Endocrinol.*, 10:87, 1996.

Cotton and Birnstiel, "Ribozyme Mediated Destruction of RNA *in vivo,*" *EMBO* J., 8(12):3861-3866, 1989.

Forster and Symons, "Self-Cleavage of Plus and Minus RNAs of a Virusoid and a Structural Model for the Active Sites," *Cell*, 49:211-220, 1987.

Haseloff and Gerlach, "Simple RNA Enzymes with New and Highly Specific Endoribonuclease Activities," *Nature*, 334:585-591, 1988.

James, "Towards Gene-Inhibition Therapy; A Review of Progress and Prospects in the Filed of Antiviral Antisense Mucleic Acids and Ribozymes," *Antisense Nucleic Acids and Ribozymes*, 2(4):191-214, 1991.

Klefstrom et al., "c-Myc Induces Cellular Susceptibility to the Cytotoxic Action of TNF-α,"p0 *EMBO J.*, 13(22):5442-5450, 1994.

Kobayashi et al., "Reversal of Drug Sensitivity in Multidrug-Resistant Tumor Cells by an MDR1 (PGY1) Ribozyme," *Cancer Research*, 54:1271-1275, 1994.

Lavrovsky et al., "Ribozyme-mediated Cleavage of the Estrogen Receptor Messenger RNA and Inhibition of Receptor Function in Target Cells," *Mol. Endocrinol.*, 13(6):925-934, 1999.

L'Huillier et al., "Efficient and Specific Ribozyme-Mediated Reduction of Bovine α-Lactalbumin Expression in Double Transgenic Mice," *Proc. Natl. Acad. Sci. USA*, 93:6698-6703, 1996.

Marshall, "Gene Therapy's Growing Pains," *Science*, 269:1050-1055, 1995.

Marshall, "Gene Therapy on Trial," *Science*, 288:951-957, 2000.

Milner et al., "Selecting Effective Antisense Reagents on Combinatorial Oligonucleotide Arrays," *Nature Biotechnology*, 15:537-541, 1997.

Pyle, "Ribozymes: A Distinct Class of Metalloenzymes," *Science*, 261:709-714, 1993.

Sarver et al., "Ribozymes as Potential Anti-HIV-1 Therapeutic Agents," *Science*, 247:1222-1225, 1990.

Scanlon et al., "Ribozyme-Mediated Cleavage of c-fos mRNA Reduces Gene Expression of DNA Synthesis and Metallothionein," *Proc. Natl. Acad. Sci. USA*, 88:10591-10595, 1991.

Stull and Szoka, "Antigene, Ribozyme and Aptamer Nucleic Acid Drugs: Progress and Prospects," *Pharmaceutical Research*, 12(4):465-483, 1995.

Suzuki et al., "Adenovirus-Mediated Ribozyme Targeting of HER-2neu Inhibits *in vivo* Growth of Breast Cancer Cells," *Gene Therapy*, 7:241-248, 2000.

Turley et al., "Vitamin E Succinate Induces Fas-Mediated Apoptosis in Estrogen Receptor-Negative Human Breast Cancer Cells," *Cancer Research*, 57:881-890, 1997.

Uhlenbeck, "A Small Catalytic Oligoribonucleotide," *Nature*, 328596-60, 1987.

Control cells

Ad/v-Rz 2 infected cells

FIG. 8B

Ad/v-Rz 2-M infected cells

FIG. 8C

SEQUENCE LISTING

<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 1
gcctggtgtg ctccgatgaa gc 22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 2
cctgcagtgg cttgctgaat cc 22

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic Oligonucleotide

<400> SEQUENCE: 3
gaugaguccg ugaggacgaa a 21

<210> SEQ ID NO 4
<211> LENGTH: 1380
<212> TYPE: DNA
<213> ORGANISM: Homo sapiens

<400> SEQUENCE: 4
ggagcccctg aaccgtccgc agctcaagat ccccctggag cggcccctgg gcgaggtgta 60
cctggacagc agcaagcccg ccgtgtacaa ctaccccgag ggcgccgcct acgagttcaa 120
cgccgcggcc gccgccaacg cgcaggtcta cggtcagacc ggcctcccct acggccccgg 180
gtctgaggct gcggcgttcg gctccaacgg cctggggggt ttcccccccac tcaacagcgt 240 gtctccgagc ccgctgatgc tactgcaccc gccgccgcag ctgtcgcctt tcctgcagcc 300
ccacggccag caggtgccct actacctgga gaacgagccc agcggctaca cggtgcgcga 360
ggccggcccg ccggcattct acaggccaaa ttcagataat cgacgccagg gtggcagaga 420
aagattggcc agtaccaatg acaagggaag tatggctatg gaatctgcca aggagactcg 480
ctactgtgca gtgtgcaatg actatgcttc aggctaccat tatggagtct ggtcctgtga 540
gggctgcaag gccttcttca agagaagtat tcaaggacat aacgactata tgtgtccagc 600
caccaaccag tgcaccattg ataaaaacag gaggaagagc tgccaggcct gccggctccg 660
caaatgctac gaagtgggaa tgatgaaagg tgggatacga aaagaccgaa gaggagggag 720
aatgttgaaa cacaagcgcc agagagatga tggggagggc aggggtgaag tggggtctgc 780
tggagacatg agagctgcca acctttggcc aagcccgctc atgatcaaac gctctaagaa 840

-continued

```
gaacagcctg gccttgtccc tgacggccga ccagatggtc agtgccttgt tggatgctga    900

gccccccata ctctattccg agtatgatcc taccagaccc ttcagtgaag cttcgatgat    960

gggcttactg accaacctgg cagacaggga gctggttcac atgatcaact gggcgaagag   1020

ggtgccaggc tttgtggatt tgaccctcca tgatcaggtc caccttctag aatgtgcctg   1080

gctagagatc ctgatgattg gtctcgtctg gcgctccatg gagcacccag tgaagctact   1140

gtttgctcct aacttgctct tggacaggaa ccagggaaaa tgtgtagagg gcatggtgga   1200

gatcttcgac atgctgctgg ctacatcatc tcggttccgc atgatgaatc tgcagggaga   1260

ggagtttgtg tgcctcaaat ctattatttt gcttaattct ggagtgtaca catttctgtc   1320

cagcaccctg aagtctctgg aagagaagga ccatatccac cgagtcctgg acaagatcac   1380
```

<210> SEQ ID NO 5
<211> LENGTH: 2092
<212> TYPE: DNA
<213> ORGANISM: Homo sapiens

<400> SEQUENCE: 5

```
gaattccaaa attgtgatgt ttcttgtatt tttgatgaag gagaaatact gtaatgatca     60

ctgtttacac tatgtacact ttaggccagc cctttgtagc gttatacaaa ctgaaagcac    120

accggacccg caggctcccg gggcagggcc ggggccagag ctcgcgtgtc ggcgggacat    180

gcgctgcgtc gcctctaacc tcgggctgtg ctctttttcc aggtggcccg ccggtttctg    240

agccttctgc cctgcgggga cacggtctgc accctgcccg cggccacgga ccatgaccat    300

gaccctccac accaaagcat ctgggatggc cctactgcat cagatccaag ggaacgagct    360

ggagcccctg aaccgtccgc agctcaagat ccccctggag cggcccctgg gcgaggtgta    420

cctggacagc agcaagcccg ccgtgtacaa ctaccccgag ggcgccgcct acgagttcaa    480

cgccgcggcc gccgccaacg cgcaggtcta cggtcagacc ggcctcccct acggccccgg    540

gtctgaggct gcggcgttcg gctccaacgg cctggggggt ttccccccac tcaacagcgt    600

gtctccgagc ccgctgatgc tactgcaccc gccgccgcag ctgtcgcctt tcctgcagcc    660

ccacggccag caggtgccct actacctgga gaacgagccc agcggctaca cggtgcgcga    720

ggccggcccg ccggcattct acaggccaaa ttcagataat cgacgccagg gtggcagaga    780

aagattggcc agtaccaatg acaagggaag tatggctatg gaatctgcca aggagactcg    840

ctactgtgca gtgtgcaatg actatgcttc aggctaccat tatggagtct ggtcctgtga    900

gggctgcaag gccttcttca agagaagtat tcaaggacat aacgactata tgtgtccagc    960

caccaaccag tgcaccattg ataaaaacag gaggaagagc tgccaggcct gccggctccg   1020

caaatgctac gaagtgggaa tgatgaaagg tgggatacga aaagaccgaa gaggagggag   1080

aatgttgaaa cacaagcgcc agagagatga tggggagggc aggggtgaag tggggtctgc   1140

tggagacatg agagctgcca acctttggcc aagcccgctc atgatcaaac gctctaagaa   1200

gaacagcctg gccttgtccc tgacggccga ccagatggtc agtgccttgt tggatgctga   1260

gccccccata ctctattccg agtatgatcc taccagaccc ttcagtgaag cttcgatgat   1320

gggcttactg accaacctgg cagacaggga gctggttcac atgatcaact gggcgaagag   1380

ggtgccaggc tttgtggatt tgaccctcca tgatcaggtc caccttctag aatgtgcctg   1440

gctagagatc ctgatgattg gtctcgtctg gcgctccatg gagcacccag tgaagctact   1500

gtttgctcct aacttgctct tggacaggaa ccagggaaaa tgtgtagagg gcatggtgga   1560

gatcttcgac atgctgctgg ctacatcatc tcggttccgc atgatgaatc tgcagggaga   1620
```

```
ggagtttgtg tgcctcaaat ctattatttt gcttaattct ggagtgtaca catttctgtc   1680

cagcaccctg aagtctctgg aagagaagga ccatatccac cgagtcctgg acaagatcac   1740

agacactttg atccacctga tggccaaggc aggcctgacc ctgcagcagc agcaccagcg   1800

gctggcccag ctcctcctca tcctctccca catcaggcac atgagtaaca aaggcatgga   1860

gcatctgtac agcatgaagt gcaagaacgt ggtgcccctc tatgacctgc tgctggagat   1920

gctggacgcc caccgcctac atgcgcccac tagccgtgga ggggcatccg tggaggagac   1980

ggaccaaagc cacttggcca ctgcgggctc tacttcatcg cattccttgc aaaagtatta   2040

catcacgggg gaggcagagg gtttccctgc cacagtctga gagctccctg gc           2092


<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence:  Synthetic
      Oligonucleotide

<400> SEQUENCE: 6

uauauguguc cagccaccaa                                                 20


<210> SEQ ID NO 7
<211> LENGTH: 41
<212> TYPE: RNA
<213> ORGANISM: Artificial Sequence
<220> FEATURE:
<223> OTHER INFORMATION: Description of Artificial Sequence:  Synthetic
      Oligonucleotide

<400> SEQUENCE: 7

uugguggcug cugaugaguc cgugaggacg aaacacauau a                         41


<210> SEQ ID NO 8
<211> LENGTH: 10
<212> TYPE: RNA
<213> ORGANISM: Artificial Sequence
<220> FEATURE:
<223> OTHER INFORMATION: Description of Artificial Sequence:  Synthetic
      Oligonucleotide

<400> SEQUENCE: 8

uauauguguc                                                            10


<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence:  Synthetic
      Oligonucleotide

<400> SEQUENCE: 9

cagccaccaa                                                            10


<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence:  Synthetic
      Oligonucleotide

<400> SEQUENCE: 10
```

-continued

```
uuauggaguc ugguccugug a                                               21


<210> SEQ ID NO 11
<211> LENGTH: 42
<212> TYPE: RNA
<213> ORGANISM: Artificial Sequence
<220> FEATURE:
<223> OTHER INFORMATION: Description of Artificial Sequence:  Synthetic
      Oligonucleotide

<400> SEQUENCE: 11

ucacaggacc acugaugagu ccgugaggac gaaacuccau aa                        42


<210> SEQ ID NO 12
<211> LENGTH: 10
<212> TYPE: RNA
<213> ORGANISM: Artificial Sequence
<220> FEATURE:
<223> OTHER INFORMATION: Description of Artificial Sequence:  Synthetic
      Oligonucleotide

<400> SEQUENCE: 12

uuauggaguc                                                            10


<210> SEQ ID NO 13
<211> LENGTH: 11
<212> TYPE: RNA
<213> ORGANISM: Artificial Sequence
<220> FEATURE:
<223> OTHER INFORMATION: Description of Artificial Sequence:  Synthetic
      Oligonucleotide

<400> SEQUENCE: 13

ugguccugug a                                                          11


<210> SEQ ID NO 14
<211> LENGTH: 42
<212> TYPE: RNA
<213> ORGANISM: Artificial Sequence
<220> FEATURE:
<223> OTHER INFORMATION: Description of Artificial Sequence:  Synthetic
      Oligonucleotide

<400> SEQUENCE: 14

ucacaggacc acuuaugagu ccgugaggac gaaccuccau aa                        42
```

ESTROGEN RECEPTOR SITE-SPECIFIC RIBOZYMES AND USES THEREOF FOR ESTROGEN DEPENDENT TUMORS

The present application is a nationalization of PCT Application Serial No. PCT/US00/15243, filed Jun. 2, 2000, which claims priority to U.S. provisional application Ser. No. 60/137,470, filed Jun. 4, 1999.

The government owns rights in the present invention pursuant to grant number from R37-AG-10488, ROI-DK-14744, and NIH Training Grant T32 AG-AG-DO165, the National Institutes of Health.

FIELD OF THE INVENTION

The present invention relates generally to the fields of cancer treatment and therapies, as a site-specific ribozyme capable of inhibiting estrogen action at the level of estrogen receptor function is disclosed. More particularly, it concerns methods for inhibiting tumor cells whose proliferation is estrogen dependent. In that the present invention also provides a therapeutic treatment, it further relates to the field of pharmaceutical preparations, particularly those directed to cancer treatment and chemotherapeutic agents. Gene therapy protocols that employ these various site-specific ribozymes are also presented.

BACKGROUND OF THE INVENTION

Estrogen receptor (ER) functions as a ligand-activated transcription factor for estrogen-regulated genes. Because of the critical role of the ER in the proliferation of certain estrogen-dependent cancer cell types such as the mammary tumor, inhibitors of estrogen action at the level of receptor function are of major clinical interest.

Estrogens are essential not only for the regulation of female reproductive functions, but also play critical roles in the propagation of a number of tumor phenotypes of estrogen target organs, such as the mammary gland. All of these hormonal functions are mediated through ERs, i.e. ER$\alpha$, Er$\beta$2. Among these receptor subtypes, ER$\alpha$ provides the dominant regulatory role in most target tissues. Primarily because of the important clinical use in the management of estrogen-dependent cancers, the search for an improved inhibitor of estrogen action has always been of significant endocrinological interest. Historically, estrogen analogs that bind to the receptor, but do not promote coactivator association and block trans-activation function, received major attention. These efforts have led to the development of several important antiestrogens, such as tamoxifen, raloxifene, and ICI 182780, all of which are used as pharmacological inhibitors of estrogen action. However, some of these antagonists also act as partial agonists, and most of them when used for a prolonged period give rise to drug resistance, possibly due to progressively increased metabolic inactivation. Additionally, the potential role of the ligand-independent constitutively active mutant forms of ER in the proliferation of certain types of cancer cells has been reported.

Alternate strategies for inhibition of ER function include a nonconventional molecular approach involving targeted overexpression of a dominant negative form of ER. This approach is based on the principle that a defective form of ER that can dimerize with the wild-type natural subunit will, upon overexpression in sufficient amounts, disable enough normal subunits and thereby inhibit the estrogen signaling cascade. The success of this approach for its therapeutic application may be dependent on massive overexpression of the defective subunit sufficient for inactivation of the wild-type receptor below a critical threshold level. Another approach is the selective intracellular destruction of ER mRNAs in target cells. Antisense ER transcripts can potentially function in this manner, and a major improvement in the antisense approach is achieved when the antisense specificity is combined with catalytic cleavage of the phosphodiester bond of the RNA target. Earlier studies with estrogen antagonists such as tamoxifen and ICI 182780 have shown that even at concentrations of 10- to 100-fold molar excesses over estradiol, these compounds can cause more than 50% inhibition of ERE-TK-Luc trans-activation and MCF-7 cell cycling. In the transient transfection assay, the ER-specific ribozymes and the hER$\alpha$ expression vector, only at an equimolar ratio, resulted in about 80% inhibition of ERE-TK-Luc trans-activation. Additionally, both of these potent antiestrogens have unique disadvantages, such as differential effects on target genes, the need for systemic administration, and the development of drug resistance after prolonged use. A need continues to exist for treatments that at least reduce and/or avoid such problems altogether in breast cancer therapies. An effective gene therapy approach for such a treatment has not yet been devised. At least in theory, such a therapy would potentially provide a targeted tissue-specific delivery of a ribozyme expression vector.

SUMMARY OF THE INVENTION

The present invention provides specially designed ribozymes that will effectively target human mRNA for estrogen receptor, effectively reducing the concentration of estrogen receptor in the cell. This in turn will slow down and inhibit estrogen receptor positive cell proliferation, such as that known to be attendant estrogen receptor positive breast cancer. By way of example, two particular ribozymes that selectively degrade the human ER mRNA and inhibit trans-activation of an artificial promoter containing the estrogen response element are disclosed in the present invention. The ribozymes of the present invention have several characteristics in common that render them especially useful in the practice of the claimed invention. These characteristics include the ability to specifically bind to a human estrogen receptor mRNA sequence, as well as having an enzymatic activity that will cleave at a position on the human estrogen reception mRNA that has an open loop region (secondary structure), and has the presence of flanking regions that are AG- or AT-rich. As used in the description of the present invention, an area that includes at least 40% of A, G and/or T, within the 20 nucleotide area down stream or upstream of the cleavage site on the mRNA target sequence, is considered to be AG or AT "rich".

The exemplary ribozymes, designated RZ-1 through RZ-7, cleave the human ER$\alpha$ mRNA at specific nucleotide positions (+377, +889, +894, +956, +1240, +1420, +1680, +1695, +1726 and +2077). They have a characteristic critical region defined by their nucleotide sequences. Even minor substitution at this region may result in significant loss of binding activity. The cleavage sites lie within the coding sequence for the DNA-binding domain of the receptor protein. The ribozyme constructs are also effective in inhibiting the progression of quiescent MCF-7 breast cancer cells to the S phase of the cell cycle after their exposure to 17$\beta$-estradiol ($10^{-9}$M).

The present invention provides a new avenue for inhibition of estrogen action by selective mRNA degradation with its therapeutic application through targeted gene delivery vectors. The present invention, more particularly, concerns the regulation of target cell function and tissue remodeling via signal transduction involving the estrogen receptor (ER). The ER belongs to the steroid, thyroid, retinoid, and vitamin D receptor superfamily of ligand-activated transcription factors. In addition to one major form of the ER, i.e. ERα, two minor subtypes, ERβ1 and ERβ2, have also been identified.

Regulation of specific gene expression by the ligand-activated ER is generally achieved in conjunction with certain coactivator proteins, whereas ER-mediated tissue remodeling requires concerted action of the receptor, other growth factors, cell cycle regulatory proteins, and apoptotic signaling agents. As estrogen-dependent reproductive abnormalities are only absent in ERα knockout and not in ERβ null mice, ERα appears to provide the critical role in most of the estrogen-regulated processes. Thus, pharmacological inhibition of ERα action provides a therapeutic control of ER-positive breast cancer cells. Much of the prior efforts in this regard have been limited to the design of estrogen analogs, which when bound to the ER prevent its access to functional estrogens. Such interactions also cause abnormal conformational change in the receptor, thereby inhibiting its trans-activational activity. Although this strategy has helped generate a number of antiestrogens, most of these compounds possess a mixed agonist/antagonist activity, and their inhibitory action may vary in a tissue- and gene-specific fashion. An alternative strategy of gene-based inhibition of ER function by dominant negative mutants of the ER is an anticipated aspect of the present invention.

Hammerhead ribozymes are provided as part of the present invention to catalyze site-specific endonuclease cleavage of the estrogen receptor mRNA. They are demonstrated to be highly effective in reducing the intracellular level of estrogen receptor mRNAs. While the invention may encompass many ribozymes useful in the practice of the invention, seven site-specific hammerhead ribozymes directed to the human (h) ERα mRNA are described in particular. These hammerhead ribozymes of the invention function by inhibiting ER function in transfected ER-negative (e.g., COS-1) cells and ER-positive (e.g., MCF-7) cells. Expression vectors containing these ribozymes provide an additional effective tool for selective inhibition of estrogen action and ER-mediated tumor cell growth both in vivo and in vitro.

Combination therapies based on antiestrogens, overexpression of the dominant negative mutants, and selective degradation of ER mRNAs, is provided as part of the present invention. This form of therapeutic method that incorporates the activity of the present invention will provide reduction and/or a virtually total blockage of estrogen action.

The hammerhead ribozymes described here, selectively inhibit estrogen action by cleaving the hERα mRNA within its DNA-binding domain. The specifier side arms of both RZ-1 and RZ-2 do not show any significant homology to any known human mRNA species, except three related receptors, hERR-1, hERR-2, and hERβ. RZ-2 possesses a slightly greater homology with hERβ (90% sequence homology with respect to both side arms) than RZ 1 (one side arm, 90%; the other, 70%). RZ-2 provides a slightly better inhibitory function on the activity of the ERE-TK-Luc plasmid in transfected MCF-7 cells than the RZ1.

The ribozymes RZ-1 through RZ-7 were designed on the basis of predicted sequence specificity with an optimum cleavage site (GUC triplet) with a region that is free of any secondary structure of the estrogen receptor mRNA structure.

Analysis of the mRNA sequence by the MFOLD computer program provides suboptimal stem-loop structures on the basis of energy minimization. However, the predicted secondary structure is only an approximation, and in the cellular context the structure may exist in a thermodynamic equilibrium of more than one conformational variation. The clonal subcellular environment and protein-RNA interactions can also significantly distort the RNA secondary structure over its minimum free energy content. Thus, ribozymes that are optimized from theoretical considerations and are effective in sequence-specific cleavage in vitro may not necessarily function with similar effectiveness within the target cell. Additionally, the stability of the ribozyme transcript is considered to be a significant complicating factor.

RZ-2, which is only about 50% as efficient as RZ-1 in the in vitro cleavage of the hERα mRNA substrate, was found to function with equal or better efficiency in inhibiting ERE-TK-Luc expression in transfected cells. The intracellular efficacy of these two ribozymes is evident not only in the inactivation of the expressed hERα cDNA transcript, but also in the inhibition of the natural hERα gene transcript in MCF-7 breast cancer cells, where the receptor mRNA undergoes normal processing steps in subcelluar compartments. It should also be noted that one of the ribozyme expression vectors that is used for this invention provides 5' capping and polyadenylation of the transcribed RNA, both of which are expected to enhance the intracellular stability of the ribozyme transcript. Finally, from the standpoint of its therapeutic application, RZ-1 and RZ-2 not only block intracellular trans-activation of the model ER target, i.e. ERE-TK-Luc, but are also effective in inhibiting a complex regulatory function such as cell cycling. The ribozyme-mediated decrease in the population of MCF-7 cells that enters into the S phase after estrogen supplementation of the quiescent cells attests to the therapeutic activity of this new class of inhibitors of estrogen action. The adenovirus-mediated regulatable gene delivery system will facilitate utilization of the ribozyme approach in therapeutic applications.

A wide variety of vectors may be employed to the practice of the present invention. By way of example and not exclusion, some of these vectors include viral vectors, such as adenovirus, adeno-associated virus, replication defective adeno-virus, vectors that have of the viral genes deleted ("gutless vectors"). Adenovirus associated virus (AAV)—derived vectors, retroviral vectors, murine oncoretrovirus, including Moloney murine leukemia virus (MMLV) or the design of these vectors may in some embodiments include the use of specific types of promoters that function to enhance the tumor—tissue site specificity of the virus for the tumor tissue. Cell-type specific, cell-cycle regulated and tumor-selective promoters, as well as promoters that respond to radiation, chemotherapy, tumor specific environmental conditions, infection by tumor viruses or specific alterations affecting the structure expression or activity of transcription factors, may also be used in the design and construction of viral vectors with the site-specific ribozyme constructs of the present invention when preparing a gene-therapy formulation.

The following sequences are used throughout the description of the present invention:

SEQ ID NO: 1=5'-GCCTGGTGTGCTCCGATGAAGC 3'

SEQ ID NO: 2=5'-CCTGCAGTGGCT-TGCTGAATCC 3'

SEQ ID NO: 3=3'-AAAGCAGGAGUGCCUGAGUAG 5'

SEQ ID NO: 4=1450 Nucleotides, positions 360–1740 of SEQ ID NO:5

Below is a truncated 1380 nt sequence of human ER mRNA starting from position #361 to # 1740:

```
 361 ggagcccctg aaccgtccgc agctcaagat ccccctggag cggcccctgg gcgaggtgta
 421 cctggacagc agcaagcccg ccgtgtacaa ctaccccgag ggcgccgcct acgagttcaa
 481 cgccgcggcc gccgccaacg cgcaggtcta cggtcagacc ggcctcccct acggccccgg
 543 gtctgaggct gcggcgttcg gctccaacgg cctggggggt ttccccccac tcaacagcgt
 603 gtctccgagc ccgctgatgc tactgcaccc gccgccgcag ctgtcgcctt tcctgcagcc
 661 ccacggccag caggtgccct actacctgga gaacgagccc agcggctaca cggtgcgcga
 721 ggccggcccg ccggcattct acaggccaaa ttcagataat cgacgccagg gtggcagaga
 781 aagattggcc agtaccaatg acaagggaag tatggctatg gaatctgcca aggagactcg
 841 ctactgtgca gtgtgcaatg actatgcttc aggctaccat tatggagtct ggtcctgtga
 901 gggctgcaag gccttcttca agagaagtat tcaaggacat aacgactata tgtgtccagc
 961 caccaaccag tgcaccattg ataaaaacag gaggaagagc tgccaggcct gccggctccg
1021 caaatgctac gaagtgggaa tgatgaaagg tgggatacga aaagaccgaa gaggagggag
1081 aatgttgaaa cacaagcgcc agagagatga tggggagggc aggggtgaag tggggtctgc
1141 tggagacatg agagctgcca acctttggcc aagcccgctc atgatcaaac gctctaagaa
1201 gaacagcctg gccttgtccc tgacggccga ccagatggtc agtgccttgt tggatgctga
1261 gccccccata ctctattccg agtatgatcc taccagaccc ttcagtgaag cttcgatgat
1321 gggcttactg accaacctgg cagacaggga gctggttcac atgatcaact gggcgaagag
1381 ggtgccaggc tttgtggatt tgaccctcca tgatcaggtc caccttctag aatgtgcctg
1441 gctagagatc ctgatgattg gtctcgtctg gcgctccatg gagcacccag tgaagctact
1501 gtttgctcct aacttgctct tggacaggaa ccagggaaaa tgtgtagagg gcatggtgga
1561 gatcttcgac atgctgctgg ctacatcatc tcggttccgc atgatgaatc tgcagggaga
1621 ggagtttgtg tgcctcaaat ctattatttt gcttaattct ggagtgtaca catttctgtc
1701 cagcaccctg aagtctctgg aagagaagga ccatatccac cgagtcctgg acaagatcac
```

SEQ ID NO:5=human mRNA sequence for estrogen receptor

```
   1 gaattccaaa attgtgatgt ttcttgtatt tttgatgaag gagaaatact gtaatgatca
  61 ctgtttacac tatgtacact ttaggccagc cctttgtagc gttatacaaa ctgaaagcac
 121 accggacccg caggctcccg gggcagggcc ggggccagag ctcgcgtgtc ggcgggacat
 181 gcgctgcgtc gcctctaacc tcgggctgtg ctctttttcc aggtggcccg ccggtttctg
 241 agccttctgc cctgcgggga cacggtctgc accctgcccg cggccacgga ccatgaccat
 301 gaccctccac accaaagcat ctgggatggc cctactgcat cagatccaag ggaacgagct
 361 ggagcccctg aaccgtccgc agctcaagat ccccctggag cggcccctgg gcgaggtgta
 421 cctggacagc agcaagcccg ccgtgtacaa ctaccccgag ggcgccgcct acgagttcaa
 481 cgccgcggcc gccgccaacg cgcaggtcta cggtcagacc ggcctcccct acggccccgg
 543 gtctgaggct gcggcgttcg gctccaacgg cctggggggt ttccccccac tcaacagcgt
 603 gtctccgagc ccgctgatgc tactgcaccc gccgccgcag ctgtcgcctt tcctgcagcc
 661 ccacggccag caggtgccct actacctgga gaacgagccc agcggctaca cggtgcgcga
```

-continued

```
 721 ggccggcccg ccggcattct acaggccaaa ttcagataat cgacgccagg gtggcagaga
 781 aagattggcc agtaccaatg acaagggaag tatggctatg gaatctgcca aggagactcg
 841 ctactgtgca gtgtgcaatg actatgcttc aggctaccat tatggagtct ggtcctgtga
 901 gggctgcaag gccttcttca agagaagtat tcaaggacat aacgactata tgtgtccagc
 961 caccaaccag tgcaccattg ataaaaacag gaggaagagc tgccaggcct gccggctccg
1021 caaatgctac gaagtgggaa tgatgaaagg tgggatacga aaagaccgaa gaggagggag
1081 aatgttgaaa cacaagcgcc agagagatga tggggagggc aggggtgaag tggggtctgc
1141 tggagacatg agagctgcca acctttggcc aagcccgctc atgatcaaac gctctaagaa
1201 gaacagcctg gccttgtccc tgacggccga ccagatggtc agtgccttgt tggatgctga
1261 gcccccccata ctctattccg agtatgatcc taccagaccc ttcagtgaag cttcgatgat
1321 gggcttactg accaacctgg cagacaggga gctggttcac atgatcaact gggcgaagag
1381 ggtgccaggc tttgtggatt tgaccctcca tgatcaggtc caccttctag aatgtgcctg
1441 gctagagatc ctgatgattg gtctcgtctg gcgctccatg gagcacccag tgaagctact
1501 gtttgctcct aacttgctct tggacaggaa ccagggaaaa tgtgtagagg gcatggtgga
1561 gatcttcgac atgctgctgg ctacatcatc tcggttccgc atgatgaatc tgcagggaga
1621 ggagtttgtg tgcctcaaat ctattatttt gcttaattct ggagtgtaca catttctgtc
1701 cagcaccctg aagtctctgg aagagaagga ccatatccac cgagtcctgg acaagatcac
1741 agacactttg atccacctga tggccaaggc aggcctgacc ctgcagcagc agcaccagcg
1801 gctggcccag ctcctcctca tcctctccca catcaggcac atgagtaaca aaggcatgga
1861 gcatctgtac agcatgaagt gcaagaacgt ggtgcccctc tatgacctgc tgctggagat
1921 gctggacgcc caccgcctac atgcgcccac tagccgtgga ggggcatccg tggaggagac
1981 ggaccaaagc cacttggcca ctgcgggctc tacttcatcg cattccttgc aaaagtatta
2041 catcacgggg gaggcagagg gtttccctgc cacagtctga gagctccctg gc
```

Requirements for ribozyme selection:

1. GUC triplet (cutting site)
2. AU-rich flanking sequence (arms).
3. Open loop structure
4. after all other requirements met, the chosen sequence has to be checked for the possible homology with sequences in other genes through gene bank. Special attention needs to be addressed to genes from steroid receptor superfamily (androgen, glucocorticoid, progesterone, etc. receptors), because they all have conservative domains (such as DNA-binding domain).

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

1A. Potential secondary structure of the hERα mRNA from 1- to 1300-nt residues encompassing the amino acid coding sequences for the N-terminal trans-activation domain, DNA-binding domain, hinge region, and part of the steroid-binding domain. Cleavage sites for the two ribozymes, RZ-1 and RZ-2, within open loop regions are indicated by arrows. 1B and 1C show the sequence structures of RZ-1 (SEQ ID NO:7, 5' to 3') and RZ-2 (SEQ ID NO:11, 5' to 3'), the complementary mRNA sequences (SEQ ID NO:6 and SEQ ID NO:10, respectively), and the expected endonuclease cleavage sites and reaction products (SEQ ID NO:8 & SEQ ID NO:9; and SEQ ID NO:12 & SEQ ID NO:13, respectively). The circled P at the cleavage product specifies the 2',3'-cyclic terminal end. Base substitutions at A→C and G→U generate catalytically inactive mutant RZ-2 (SEQ ID NO:14). The expected points of cleavage at the mRNA sequence are indicated by arrowheads.

Figure 1A:
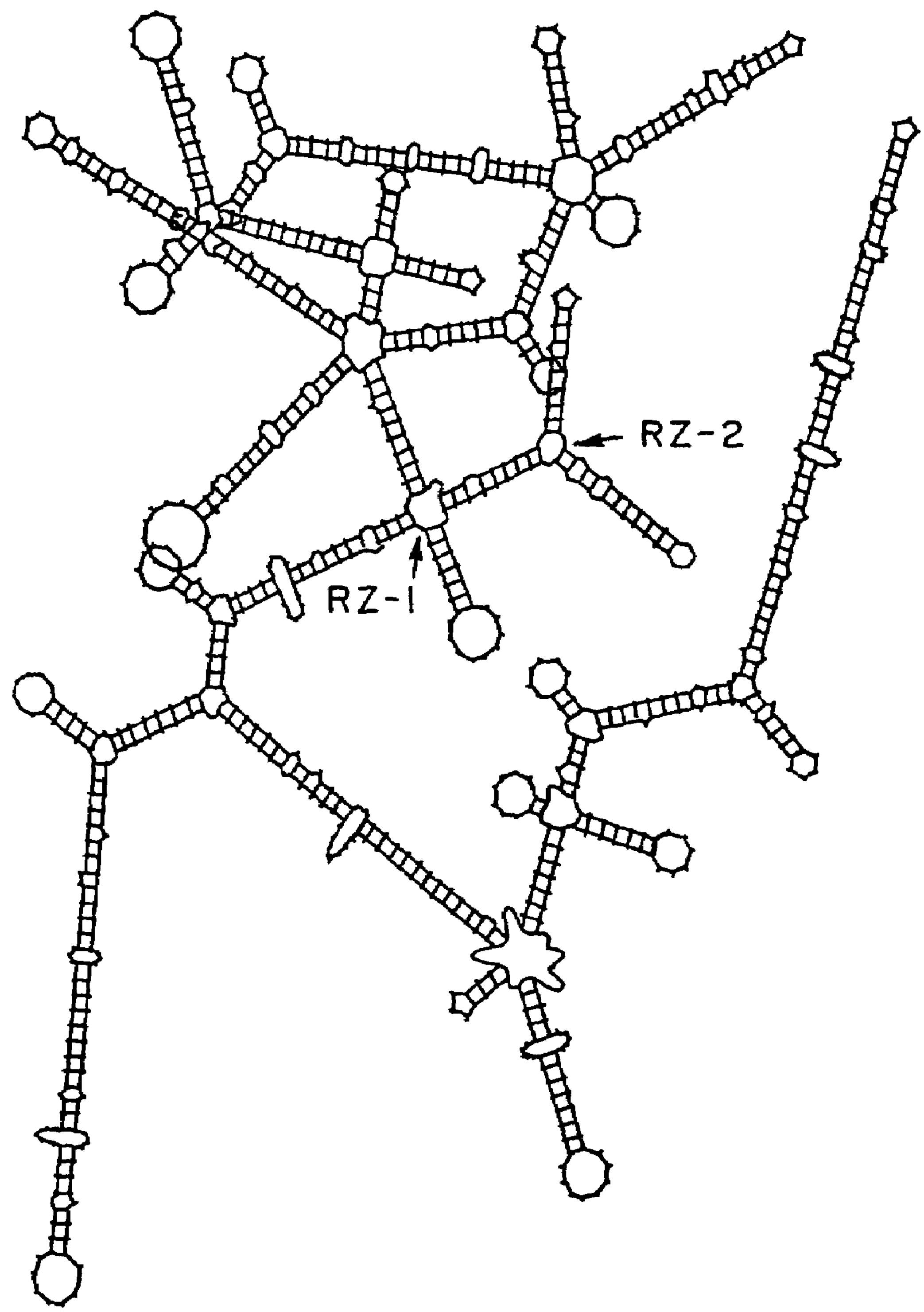
FIGS. 1A–1C. Stem-Loop Secondary Structure of the hERα mRNA and the Nucleotide Sequence of Two hERα-Specific Hammerhead Ribozymes.
Figure 1B:
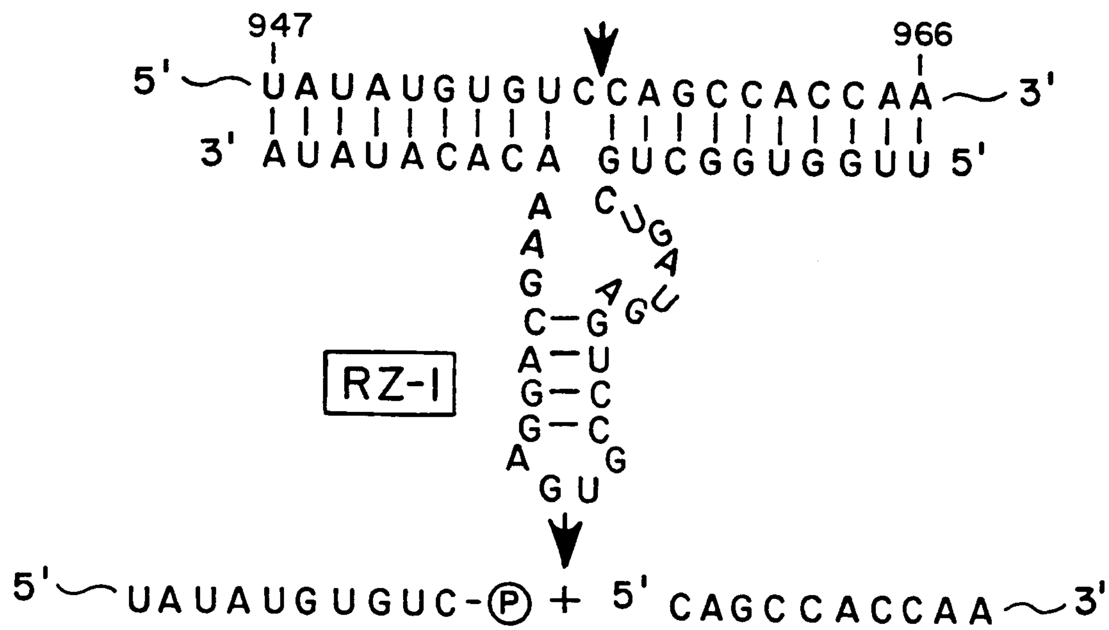

FIGS. 2A–2D. Site-Specific Endonuclease Activity of RZ-1 and RZ-2 on a 390-nt Long hERα mRNA Fragment 2A and 2B. Time course of the cleavage reaction of an equimolar mixture of the RNA substrate and RZ-1 (A) and RZ-2(B), respectively, after, 5, 15, 30, 60, 90, and 120 min of incubation (lanes 1–7). 2C, PhosphorImager quantification of the cleavage kinetics of the RZ-1 (filled circles) and RZ-2 (empty circles). 2D, lanes 1–3, Cleavage pattern produced by RZ-1 or RZ-2 singly or by a 50:50 mixture of the two ribozymes after 60 min of incubation. Lane 1, RZ-1; lane 2, RZ-2; lane 3, RZ-1 plus RZ-2. The substrate and reaction products in nucleotide residues are indicated with arrows. Lanes 4–7 show the results of control experiments. Lanes 4 and 5 correspond to reactions with mutant RZ-1 and mutant RZ-2, respectively, using the same $^{32}$P-labeled ER2 substrate as in lanes 1–3. Both mutants contain two-point mutations at the catalytic core (as shown in FIG. 1), and in neither case was cleavage product generated. Lanes 6 and 7, the $^{32}$P-labeled glucocorticoid receptor (GR) mRNA substrate incubated with RZ-1 (lane 6) and RZ-2 (lane 7). The probe position corresponding to the GR mRNA substrate is shown by the arrow at the right coiner of the panel.

Figure 3A:
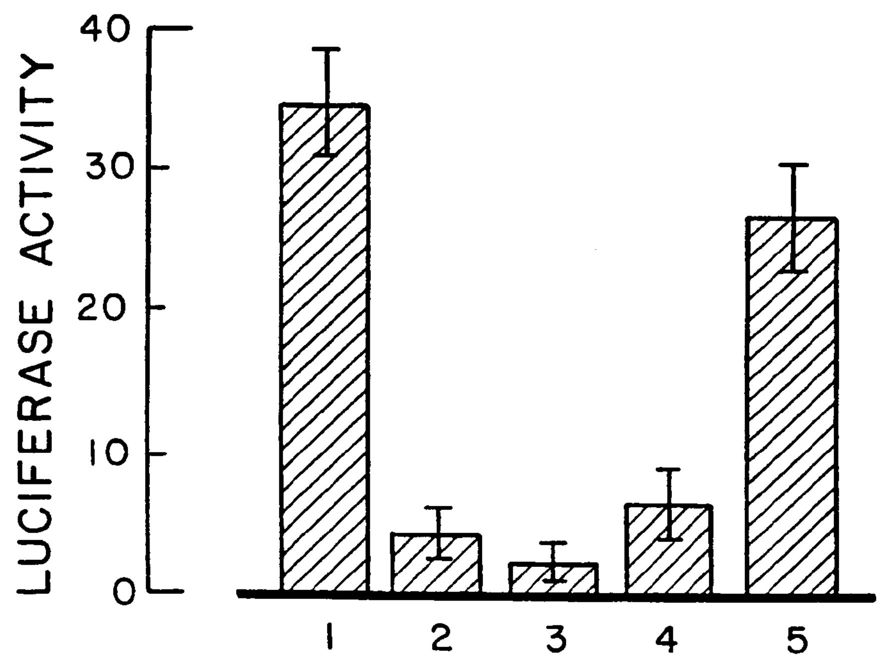
Figure 3B:
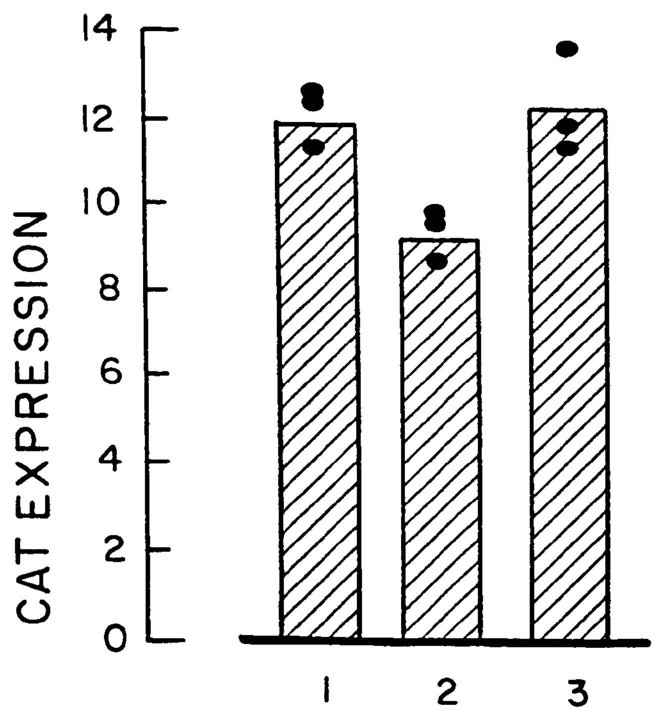

FIGS. 3A–3B. Ribozyme-Mediated Inhibition of the *Xenopus* Vitallogenin Promoter-Derived ERE (3A) and MMTV Long Terminal Repeat (3B) Activation in Transfected COS-1 cells.

Figure 4:
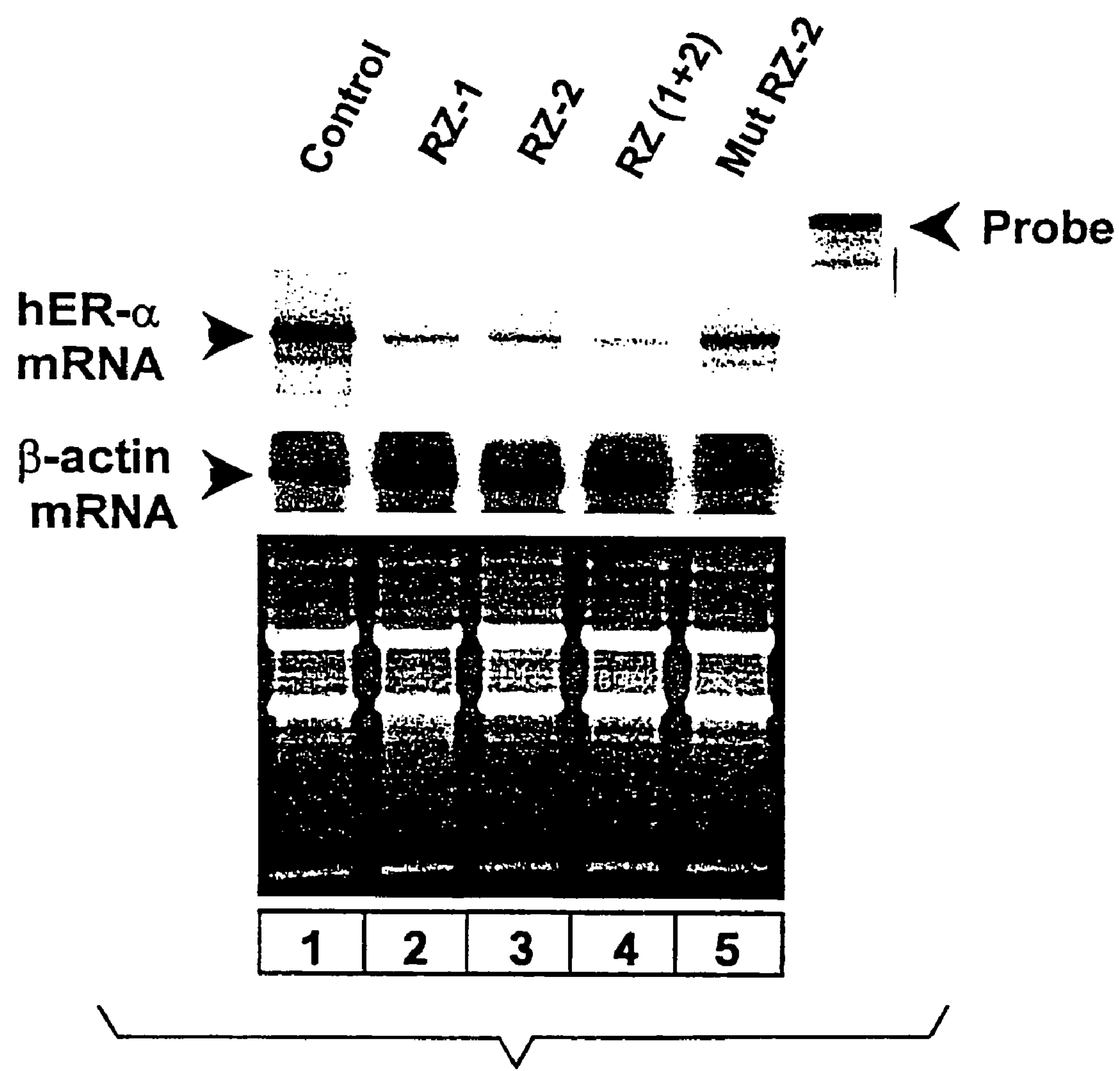

FIG. 4. Quantitative Analysis of the hERα mRNA by RNase Protection Assay in COS-1 Cells Co-Transfected with hERα and Ribozyme Expression Vectors.

RNA samples were derived from cells transferred with the hERα expression vector and pcDNA3.1 (control lane 1) and hERα expression vector along with a 10-fold molar excess of ribozyme vectors as indicated on the top. The upper frame shows the autoradiogram of the hERα mRNA-protected antisense probe, the middle frame shows an autoradiogram of the β-actin mRNA (invanant control)-protected antisense probe, and the bottom frame shows 5 μg total RNA samples from the corresponding cells, separated electrophoretically on a nondenaturing agarose gel and stained with ethidium bromide.

(FIG. 4, middle and bottom panels, respectively). From these results, expression of either RZ-1 or RZ-2 transcripts can cause selective degradation of the hERα mRNA, thereby reducing the ERα protein level in transfected cells, which, in turn, is reflected in the decreased activity of the ER-responsive promoter-reporter construct.

Figure 5:
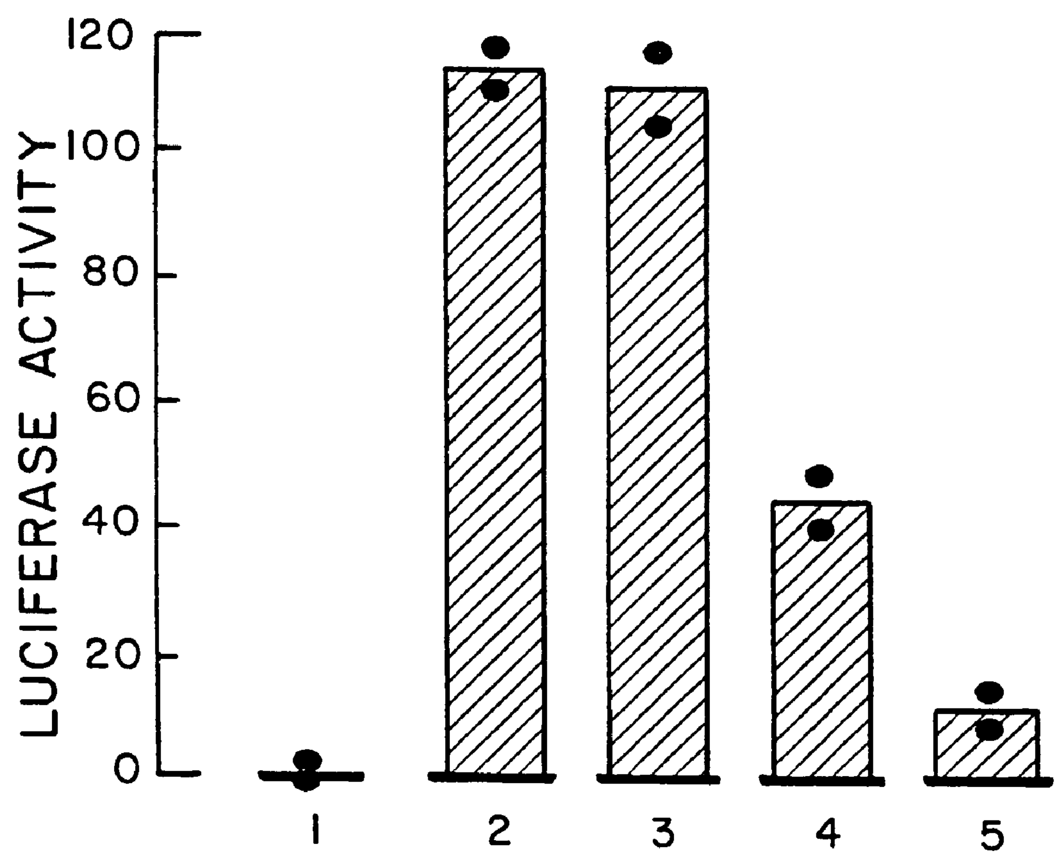

FIG. 5. Inhibition of the Endogenous ER-Mediated Trans-Activation of the ERE-TK-Luc in Transfected MCF-7 Cells FIG. 6. Relative PI Fluorescence. Flow Cytometric Analysis of the S Phase Cell Population in MCF-7 Cells Transfected with the Ribozyme Expression Vector.

Figure 7:
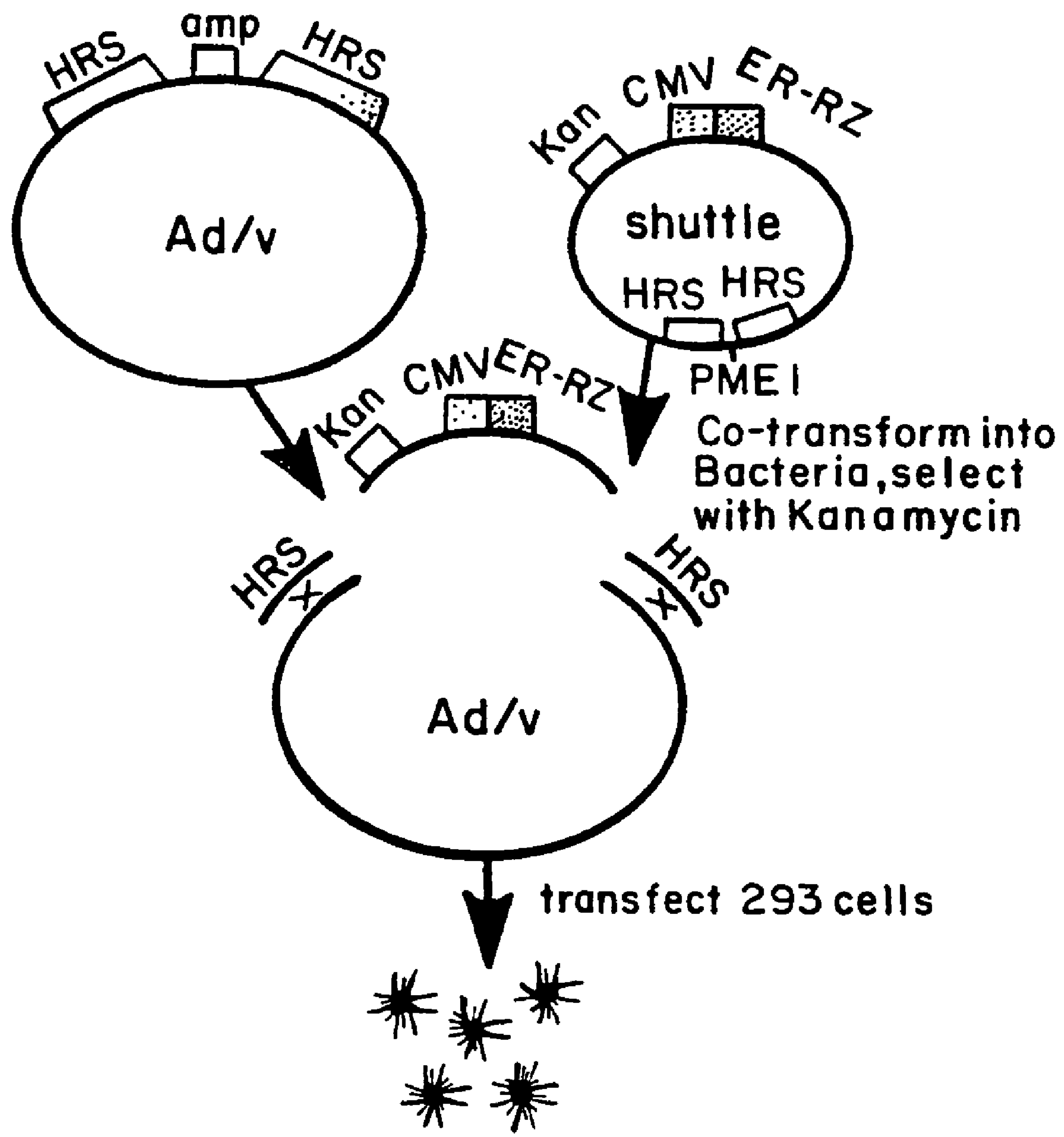

FIG. 7. Schematic presentation of adenovirus-based system for delivery of estrogen receptor-specific ribozyme (ER-RZ). HRS: homologous recombination site. Ad/v: adenoviral "backbone plasmid". CMV: promoter region of cytomegalovirus. PME I: a unique restriction site.

Figure 8A:
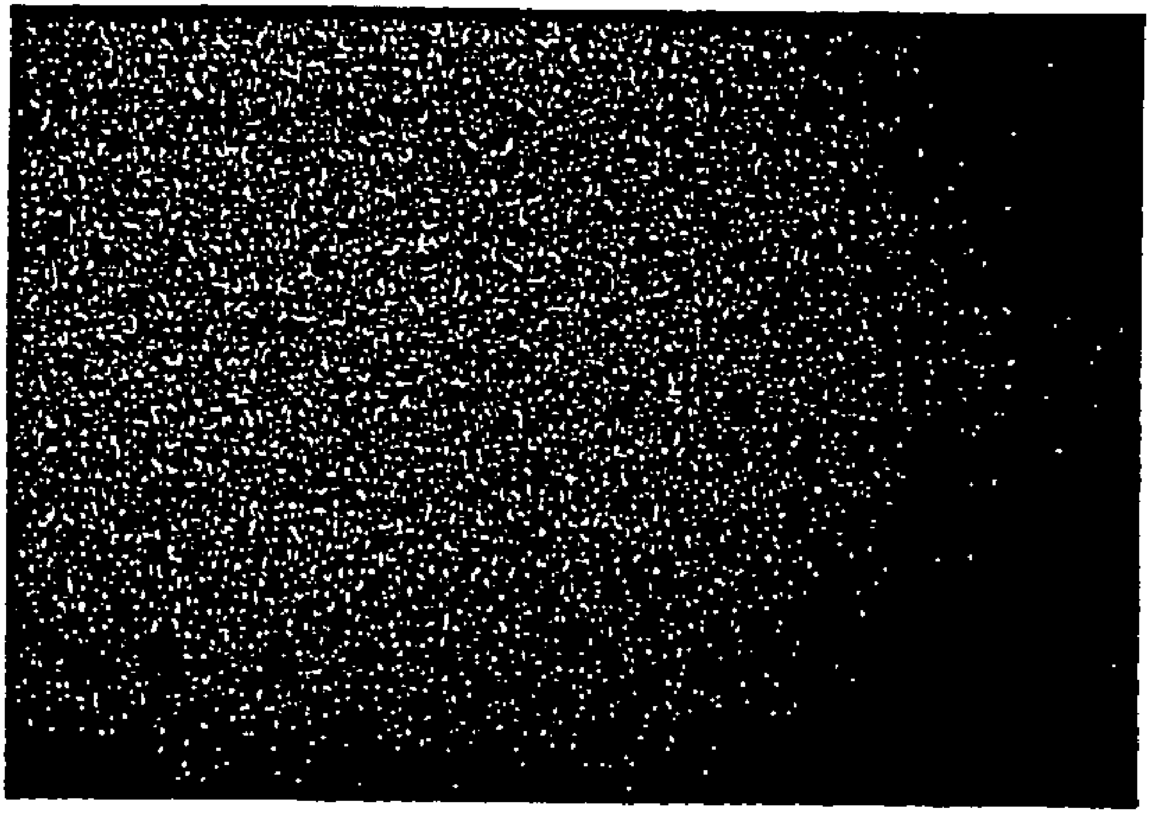
Figure 8B:
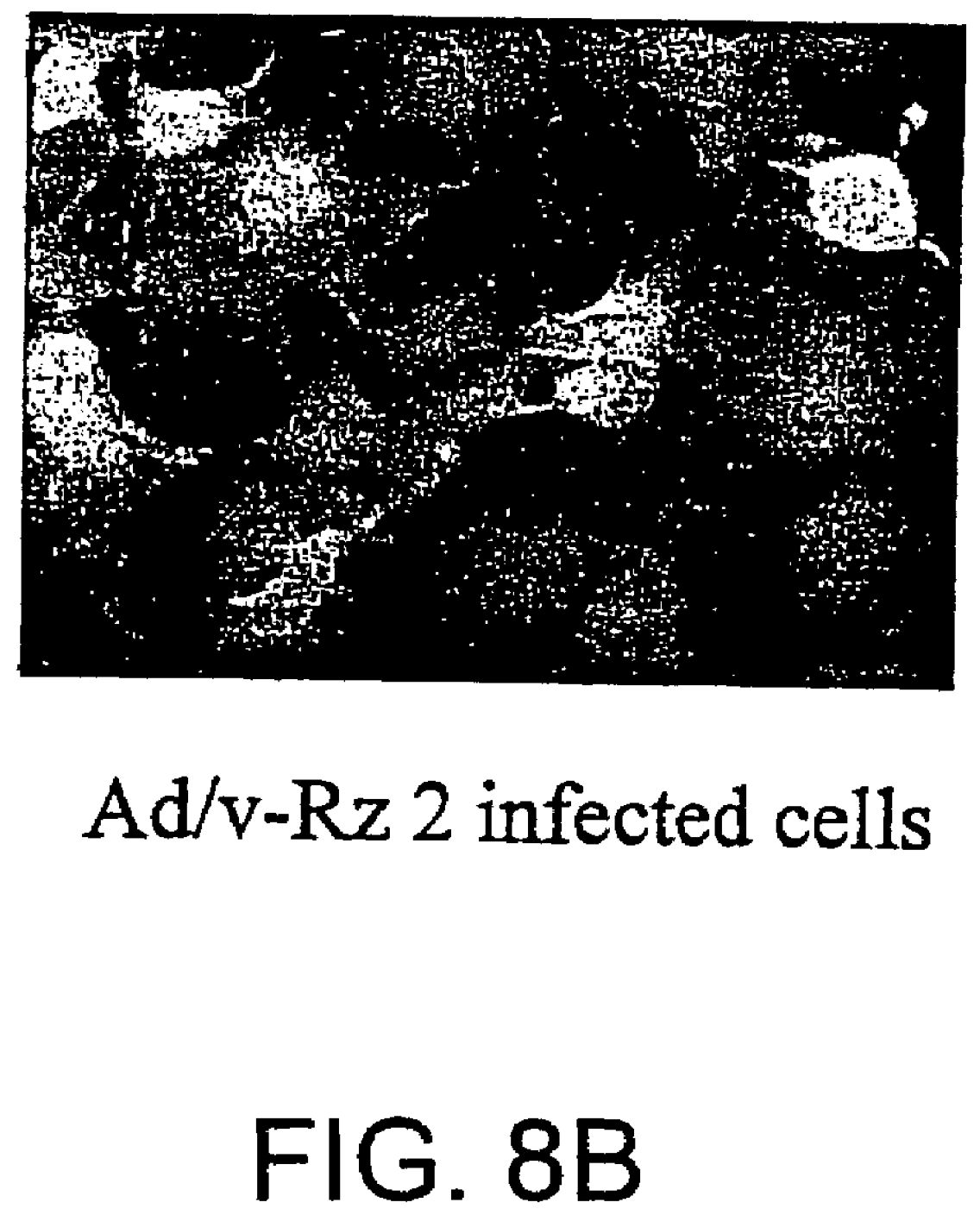
Figure 8C:
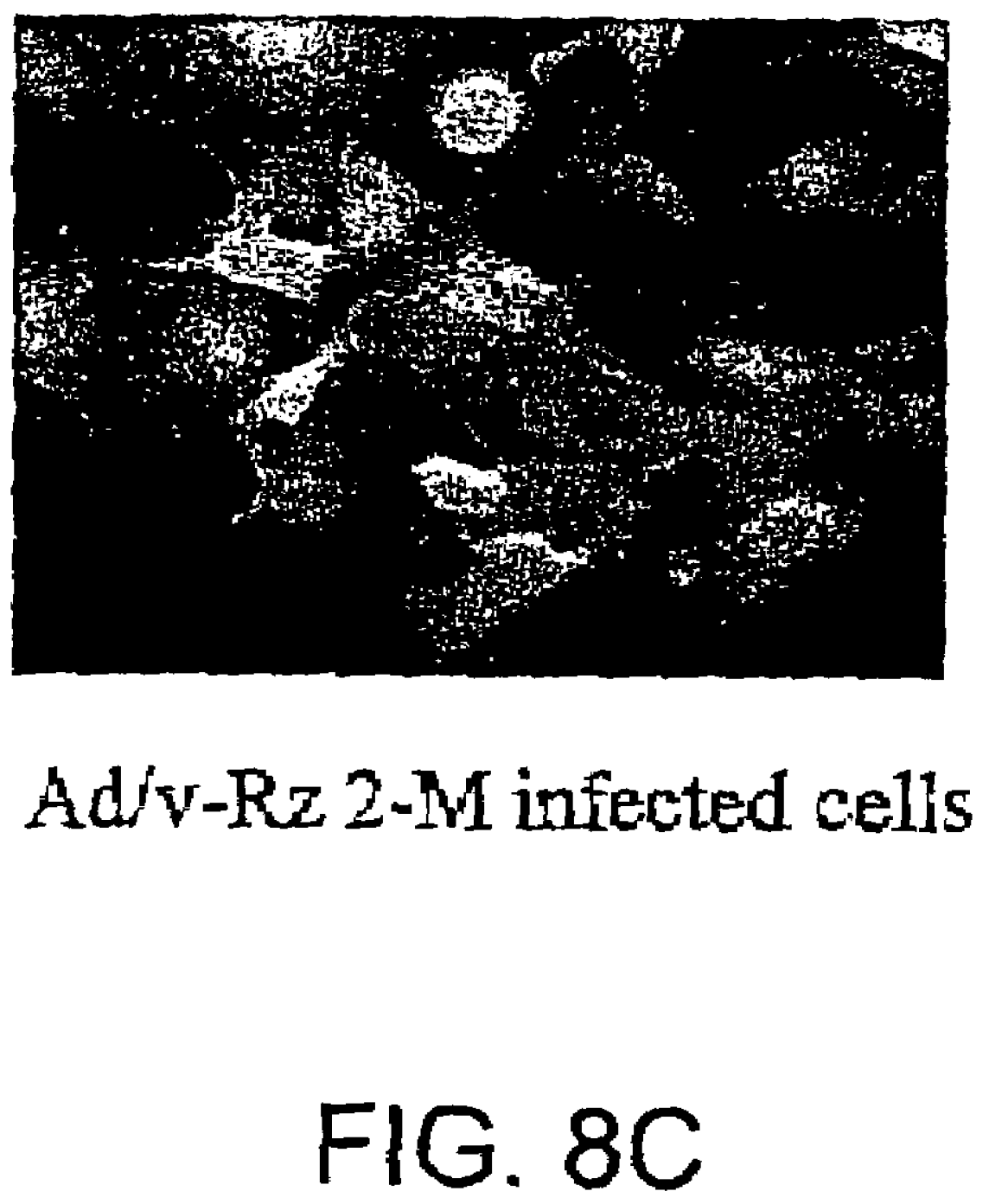

FIGS. 8A, 8B, 8C. Human breast adenomacarcinoma MCF-7 cells were seeded into 35 mm plates and infected with adenovirus containing $10^6$ pfu/ml of wild-type or mutant estrogen receptor-specific ribozymes (Ad/v-RZ 2 and Ad/v-RZ 2-M). Images were taken 24 hours after infection. Infection efficiency was estimated according to the amount of green fluorescent protein (GFP) produced by the cells. GFP gene is a part of the adenoviral vector and serves as a marker of expression. An experiment assessing an efficiency of Ad/v-Rz 2-specific cleavage of the ERα mRNA is being currently conducted. FIG. 8A Control. Cells (no adenovirus infection); FIG. 8 B=Ad/v-RZ2 infected cells (Cells infected with adenovirus containing estrogen receptor-specific ribozyme-2) FIG. 8C=Ad/v-RZ 2 M infected cells (cells infected with adenovirus containing mutant estrogen receptor-specific ribozyme.

DETAILED DESCRIPTION OF THE PREFERRED EMBODIMENTS

Following long-standing patent law convention, the terms "a" and "an" mean "one or more" when used in this application, including the claims.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Selection of Ribozyme Target Sites

Based on the primary and secondary structure analysis of the hERα mRNA sequence, an optimum target site for each hammerhead ribozyme was chosen. The sites free of any potential secondary structure were identified by analysis of the ERα mRNA sequence using the MFOLD program (Genetics Computer Group, version 8.1, Madison, Wis.) which predicts optimal and suboptimal RNA secondary structures based on the energy minimization method. The linear structure of the mRNA was converted into a two-dimensional stem-loop format by processing the results of the MFOLD analysis in a VAX computer using the SQIGGLES graphic program. The structure containing the least free energy change of formation was used for further consideration. To eliminate non-ERα mRNA targets, approximately 20-nucleotide sequence stretches surrounding GUC triplets within the single-stranded, looped regions of the two-dimensional structure were selected by the present invention, and those sequences that lack any substantial homology with non-ER mRNA sequence in the GenBank database were selected.

EXAMPLE 2

Expression Constructs for Ribozymes and ERα

Oligodeoxynucleotides corresponding to the wild-type RZ-1 and RZ-2 as well as the corresponding mutant ribozymes were synthesized at an institutional DNA synthesis core facility, and the oligos were purified on a 16% polyacrylamide/8 M urea gel. The Bluescript SK plasmid (Stratagene, La Jolla, Calif.) was digested with Sac1 and EcoRl restriction enzymes, and each oligonucleotide was subcloned into the plasmid vector via the Sac1/EcoRl cloning sites. The human ERα mRNA fragment from 748–1047 nucleotide positions (GenBank accession no. M12674) was used as the substrate for the ribozyme-catalyzed cleavage reaction. In vitro transcription by T7 RNA polymerase was employed to synthesize the RNA substrate from the cDNA template spanning positions 748–1047 of the human ERα mRNA. RT-PCR of the total mRNAs of MCF-7 cells in the presence of appropriate sense and antisense primers (each 20 nucleotides long), and cloned into the plasmid vector pGEM-TEasy (Promega Corp, Madison, Wis.) to generate Teasy-ER plasmid. To generate the mRNA substrate corresponding to the GR DNA-binding domain (+1387+–1642, GenBank accession no. M14063), the cDNA was amplified using GR-specific primers (5'-GCCTGGTGTGCTCCGATGAAGC (Seq. ID. No.:1) and 5'CCTGCAGTGGCT-TGCTGAATCC), (Seq. ID. No.:2) and the 256 bp PCR product was subcloned into the pCRII cloning plasmid (Invitrogen). The radiolabeled RNA substrate was synthesized by T7 RNA polymerase-directed in vitro transcription of BamHI-digested plasmid construct in the presence of [$\alpha^{32}$ P]UTP. An expression construct for this full-length human ER$\alpha$ cDNA driven by the Rous sarcoma virus long terminal repeat (RSV-ER) was used to assess ribozyme function in transfected COS-1 cells. The GR expression plasmid was driven by the cytomegalovirus (CMV) promoter. The original full-length GR cDNA clone was obtained from American Type Culture Collection (Manassas, Va.) and was subsequently cloned into the plasmid pCMVS. Luciferase expression from the plasmid ERE-TK-Luc containing the virtellogenin ERE ligated to the luciferase reporter gene provided measures of ER functionality in transfected cells. Ribozyme expression in transfected cells was driven by the CMV promoter of the ribozyme expression plasmids, which were produced by cloning the ribozyme sequences (wild-type) and mutant) into pcDNA3.1 (Invitrogen, San Diego, Calif.). All constructs were authenticated by DNA sequencing.

EXAMPLE 3

Substrate Cleavage in Vitro by Ribozymes

A radiolabeled RENA substrate was prepared by T7 RNA polymerase-directed in vitro transcription of the Sal-digested Teasy-ER plasmid in the presence of [$\alpha$-$^{32}$P]UTP and the other three unlabeled d-NTPs using conditions described herein. The hammerhead ribozyme transcripts were synthesized from the EcoRI-digested ribozyme expression constructs by in vitro transcription directed by T7 RNA polymerase. The in vitro cleavage reactions were performed as described herein with some modifications. Briefly, the radiolabeled mRNA substrate and the ribozyme(s) were separately preincubated at 37° C. for 3 min in 50 mm Tris-HCl (pH 7.5), 2 mm spermine, and 1 mm EDTA. Each preincubated mixture was then brought to 10 mm $MgCl_2$ and mixed together to initiate the cleavage reaction by incubation at 37° C. At the end of the incubation, the reaction products along with 5 microgram yeast transfer RNA (carrier) were precipitated at −70° C. (30 min) in the presence of 2.5 M ammonium acetate and 70% ethanol and once with absolute ethanol, and then air-dried. The dry pellets were suspended in a RNA sample buffer containing 10 mm EDTA, 90% formamide, 0.1% bromophenol blue, and 0.1% xylene cyanol and heated for 5 min at 95° C. Afterward, the cleavage products were resolved electrophoretically on a 5% polyacrylamide/8 M area gel. The products along with the uncleaved substrate were visualized by autoradiography. To monitor the kinetics of the enzymatic cleavage, 100 ul of a mixture containing the unlabeled ribozyme and the $^{32}$P-labeled ER mRNA substrate (1:1 molar ratio) were incubated at 37° C.; reaction mixtures were removed in aliquots at different time points, precipitated and processed as described herein. The percentage of cleavage was quantified by Phosphorimager (GS-363, Bio-Rad Laboratories, Inc., Richmond, Calif.) analysis of the—radiolabeled bands after subtracting background values.

Cell Transfection

MCF-7 (ER-positive) and COS-1 (ER-negative) cells were obtained from American Type Culture Collection and cultured in serum-containing medium as recommended by the supplier. The COS-1 cells were plated in six-well culture flasks at 2×10$^5$ cells/well, grown overnight, and then, using the LipoTaxi (Stratagene) reagent, cotransfected with the ERE-TK-Luc reporter construct, pRSV-ER target vector, and the ribozyme expression construct. After 4 h, the cells were placed in the growth medium (MEM and phenol red-free, 5% charcoal-stripped FBS) with or without $10^{-9}$ M 17$\beta$-estradiol. At the end of 48 h, the cells were harvested, and cell extracts were assayed for luciferase activity (assay kit, Promega Corp.), and protein concentrations were determined by the Bradford procedure. The MMTV-CAT plasmid was used as the reporter construct to examine the effect of the ribozyme on GR-activated reporter expression in COS-1 cells, using transfection conditions similar to those described above in the presence or absence of dexamethasone ($10^{-8}$ M). The cell extracts were assayed for CAT expression by enzyme-linked immunosorbent assay using 50 microgram protein extracts according to the manufacturer's protocol (Boehringer Mannheim, Indianapolis, Ind.). Results were expressed as optical densities (×1000) per microgram protein. For RNase protection, COS-1 cells were seeded in T75 flasks (~1×10$^6$/flask), cultured overnight, and transfected with the ER expression plasmid and appropriate ribozyme expression constructs. To achieve the highest possible transfection efficiency for the flow cytometric analysis of MCF-7 cells, the high efficiency FuGENE6 (Boehringer Mannheim) transfection reagent was used.

RNase Protection

Total RNA from transfected cells was isolated using the RNeasy Kit (QIAGEN, Chatsworth, Calif.). The antisense probe for hER$\alpha$ mRNA was generated by SP6 polymerase-directed in vitro transcription of the NcoI-digested Teasy-ER plasmid construct in the presence of [-$^{32}$P]UTP and three other d-NTPs, and RNase protection was performed using an RPAII assay kit (Ambion, Inc., Houston, Tex.). The $\beta$-actin antisense RNA probe was used as an internal control. Radiolabeled bands were quantitated by Phosphorimager analysis.

Flow Cytometry

Cell cycle distributions of the ribozyme-expressed and control vector-expressed MCF-7 cells were examined by FACS analysis of the propidium iodide-stained cell. MCF-7 cells were seeded in T75 flasks at about 0.5×10$^6$ cells, cultured overnight, and then transfected with 10 ug plasmid using 20 µi FuGENES transfection reagent (Boehringer Mannheim) according to the manufacturer's recommended protocol. At the end of 12 h of transfection, the cells were washed and placed in fresh culture medium containing 1 nM 17$\beta$-estradiol. The cells were cultured for an additional 26 h and harvested for analysis by flow cytometry. The harvested cells were pelleted, washed with PBS (pH 7.5), and incubated with 500 µl 70% ethanol at −20° C. for 2.5 h. After washing with PBS containing 0.5% BSA, the pelleted cells were resuspended in 150 µl fresh PBS. To the cell suspension were added 1 vol propidium iodide (100µ/ml) and 0.5 vol RNase A solution (1 mg/ml), and the stained cells were filtered through nylon mesh. The cells were then analyzed in a FACS (FACStar Plus, Becton Dickinson and Co.). Data were analyzed using the ModFit Lt program (Verit/ml) and 0.5 vol RNase A solution (1 mg/ml), and the stained cells were filtered through nylon mesh. The cells were then analyzed in a FACS (FACStar Plus, Becton Dickinson and Co.). Data were analyzed using the ModFit Lt program (Verit House Software).

EXAMPLE 4

Figure 1C:
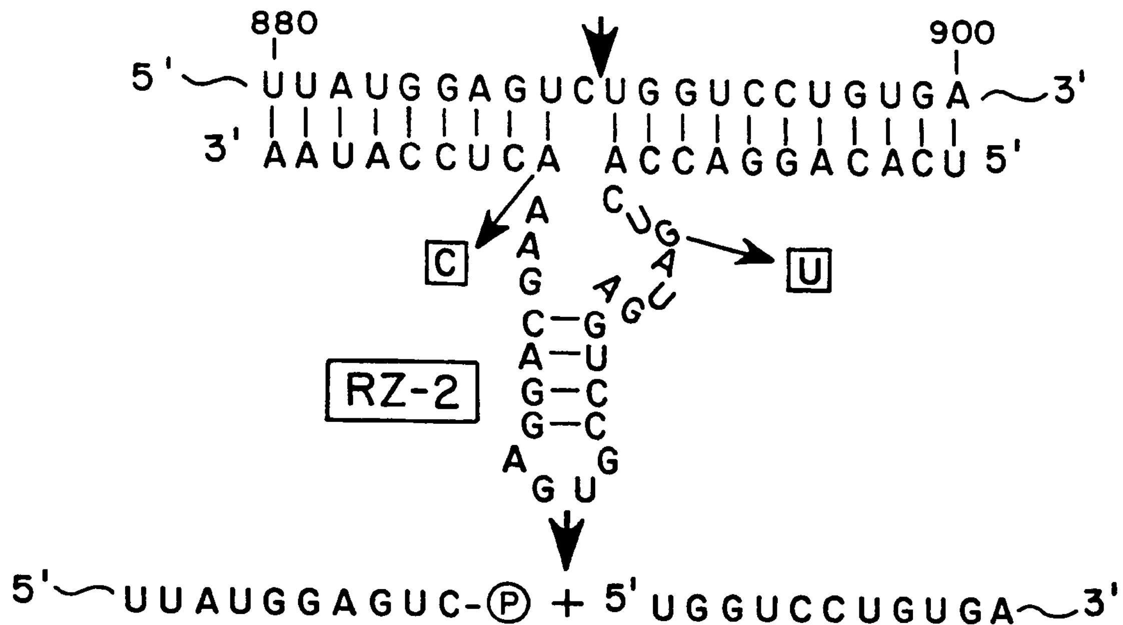

Design of the Human ERα-Specific Hammerhead Ribozymes and Selection of Accessible and Optimum Cleavage Sites Among various types of catalytic RNAs, the trans-acting hammerhead ribozyme provides certain advantages as a tool for selective degradation of the eukaryotic messenger RNA. Among other reasons, this is due to their high intrinsic catalytic rate and small overall size. The hammerhead ribozyme consists of three distinct components: a central catalytic core and two variable side arms that direct site-specific duplex formation with the corresponding substrate mRNA. The length of the two side arms and their A-U to G-C ratio determine the rate of turnover of the ribozyme after a single round of catalytic reaction. Optimum catalytic cleavage occurs at the end of GUC triplet, producing a 2',3'-cyclic phosphate and a 5'-terminus. To provide the highest accessibility of the ribozyme to the hERα mRNA, the potential secondary structure of the hERα mRNA sequence was examined through the energy minimization approach. FIG. 1A shows the potential stem-loop configuration of the hERα mRNA from nucleotide positions +1 to +1300 encompassing coding sequences for the N-terminal trans-activation domain, DNA-binding domain, hinge region, and part of the steroid-binding pocket. Based on the computer search of the looped regions with GUC triplets and at least 50% AU contents, two potential cleavage sites for the ribozyme at positions +889 and +956 were selected. Cleavage sites of these ribozymes, ribozyme-1 (RZ-1) and ribozyme-2 (RZ-2) are indicated with arrows in FIG. 1A. The optimum substrate specificity and turnover rate was determined by the present inventors to be achievable with two side arms of 9–11 residues each and with a close to 50% A-U base pairs at the RNA—RNA duplex. The sequence structures of RZ-1 and RZ-2 are shown in FIGS. 1, B and C, respectively. GenBank search of the binding region of RZ-1 (hERα sequences from +947 to +966) and RZ-2 (hERα) sequences from +880 to +900 indicated the absence of significant homology of these two sequence regions of the hERα mRNA to any known human mRNAs, except for hERβ and ER-related orphan receptors hERR-1 and hERR-2. The present inventors determined that substitution of two bases at the catalytic core of the hammerhead ribozyme (A→C and G→U, as indicated in FIG. 1C) causes an almost total loss of the catalytic activity without any significant change in base pairing capacity. The present inventors designed mutant ribozymes with the two above-mentioned base substitutions to distinguish the intracellular effects of antisense and catalytic functions. These ribozymes were then tested for their catalytic activities in vitro.

EXAMPLE 5

Catalytic Cleavage of the hERα mRNA Substrate by RZ1 and RZ-2

Figure 2A:
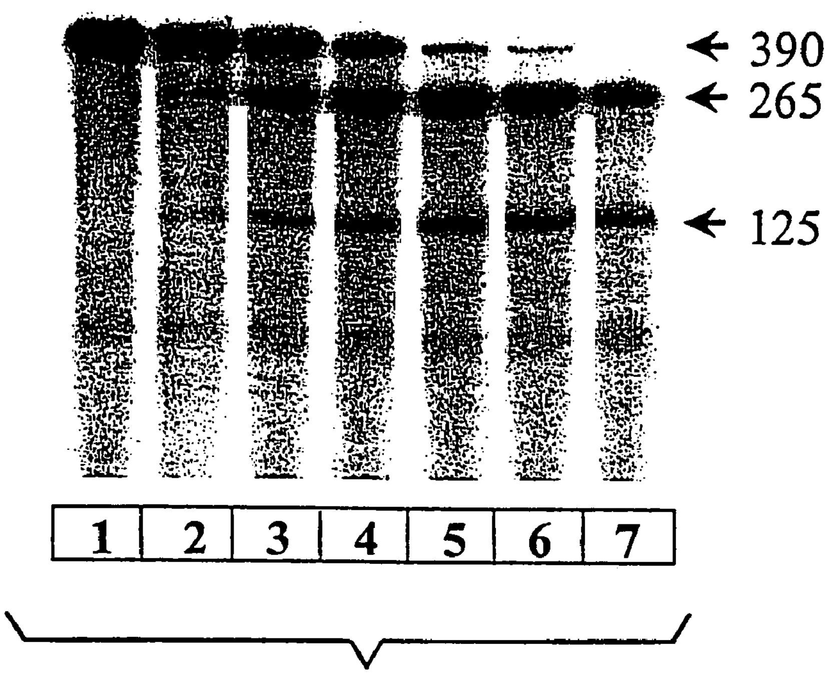
Figure 2B:
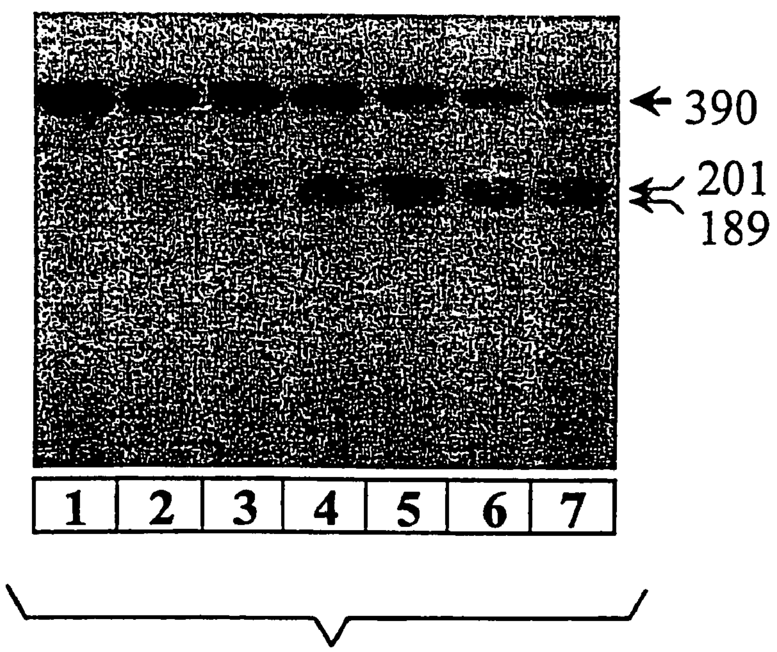
Figure 2C:
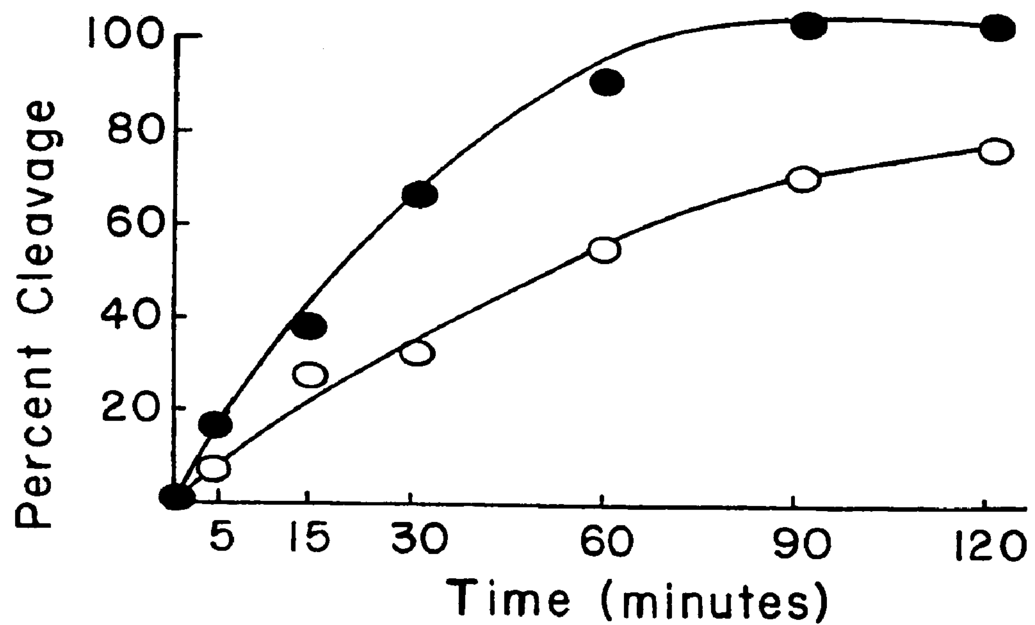
Figure 2D:
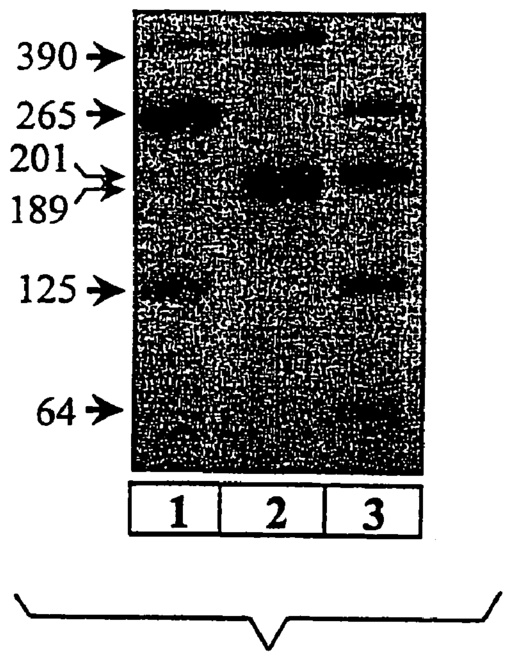

Ribozymes were synthesized by in vitro transcription of the corresponding recombinant genes, and their specificity and catalytic activities were examined on $^{32}$P-labeled RNA substrates. For hERα, a 390-nucleotide (nt) long mRNA substrate containing the expected cleavage sites for both ribozymes was used as the substrate target. Electrophorectic autoradiograms of the cleavage reaction catalyzed by RZ-1 and RZ-2 are displayed in FIGS. 2A and 2B. The results show that both of these ribozymes cleaved the mRNA substrate in a highly sequence-specific fashion. RZ-1 produced two cleavage products of the expected sizes (267 and 125 nt) from the 390-nt long hER-α mRNA substrate (FIG. 2A). Similarly, the same substrate was cleaved by RZ-2 to yield 201- and 189-nt long reaction products, as expected from the site of excision at the end of the GUC triplet at the +889 position. Based on the time course of the cleavage reaction, it appears that RZ-1 (FIG. 2A) is about twice as effective in vitro as RZ-2 (FIG. 2B). In the case of RZ-1, at an equimolar ratio of substrate to ribozyme, 50% of the mRNA substrate was converted to reaction products within 25 min of incubation. RZ-2 takes about 50 min to achieve 50% cleavage of the mRAN substrate (FIG. 2C). Additionally, when RZ-1 and RZ-2 are allowed to function together in vitro on the same substrate, they do not appear to affect each other either in a positive or negative manner (FIG. 2D, lane 3). The results presented in FIG. 2D, lane 3, also show that one of the reaction products of RZ-1 (189 nt long) containing the RZ-2 cleavage site was further cleaved into 125- and 64-nt RNA fragments. Two base substitutions (as indicated in FIG. 1C) within the catalytic core of RZ-1 and RZ-2 almost completely abolished their enzymatic activities (FIG. 2D, lanes 4 and 5). Additionally, neither of these ribozymes displayed any significant degree of endonuclease activity on an mRNA fragment containing the corresponding DNA-binding domain of the glucocorticoid receptor (GR; FIG. 2D, lanes 6 and 7). Collectively, these results demonstrate the high degree of catalytic activity and substrate specificity of the two ribozymes.

EXAMPLE 6

Inhibition of Estrogen Response Element (ERE)—Containing Promoter Function and Decrease in hERα Transcripts in COS-1 Cells Contransfected with hERα and Ribozyme Expression Constructs COS-1 cells are ER negative, and they can be made estrogen sensitive by transient transfection with an ER expression vector). When COS-1 cells were transfected with the hERα expression plasmid along with a promoter-reporter construct containing the ERE from the vitollogenin gene promoter and the luciferase-coding sequence, the cells became estrogen sensitive (FIG. 3A, bar 1). The addition of either RZ-1 (bar 2) or RZ-2 (bar 3) expression vectors caused more than 80% reduction in luciferase activities. As expected from the in vitro cleavage reaction, a 50:50 mixture of RZ-1 and RZ-2 did not show any significant difference in the inhibition of the estradiol-ER-dependent increase in luciferase activity (bar 4). The mutant form of RZ-2 (bar 5) caused only about 20% inhibition of the promoter function, possibly due to its antisense effect on the hERα transcript. The results presented in FIG. 3B show that COS-1 cells, when transfected with a GR expression plasmid, showed no significant inhibition of dexamethasone-induced chloramphenicol acetyltransferase (CAT) expression from the mouse mammary tumor virus (MMTV)-CAT promoter-reporter after cotransfection with either RZ-1 or RZ-2. The ribozyme-mediated decrease in luciferase activity in transiently transfected COS-1 cells is indeed due to a concomitant decrease in the hERα mRNA level. This was indicated by the results of the ribonuclease (RNase) protection assay (FIG. 4). RZ-1, RZ-2, and RZ-1 plus RZ-2 all caused declines in the level of the hERα mRNA-protected radiolabeled antisense band to approximately 80%, and the mutant RZ-2 was only weakly effective (FIG. 4, upper panel). No significant difference in the intensity of the protected bands resulting from the β-actin control antisense probe can be seen, and the overall quality of the total cellular RNA remained unaltered after ribozyme transfection.

Luciferase activities are expressed as arbitrary light units per μg protein, and CAT values as optical densities×$10^3$ per μg protein. A. The cells were cotransfected with the hERα expression vector (1 μg), ERE-TK-Luc promoter-reporter vector (1 μg), and either the ribozyme expression vector (1 μg) or the same amount of the empty express vector (pcDNA3.1). Luciferase activity was determined at 48 h after transfection. All culture media except the negative control contained $10^{-3}$ M 17 β-estradiol. The numbers on histograms represent reporter activity (minus the background activity of the estrogen-free negative control containing the hERα expression vector) derived from cells transfected with the following expression vector combinations: 1, ERE-TK-Luc and hERα; 2, ERE-TK-Luc, hERα, and RZ-1; 3, ERE-TK-Luc and hERα+RZ-2; 4, ERE-TK-Luc. hERα, and a 50:50 mixture of RZ-1 plus RZ-2; 5, ERE-TK-Luc. hERα, and mutant RZ-2. Each histogram is a mean of four determinations ±SD. B, Cells were transfected with the GR expression vector (1 μg) and the reporter MMTV-CAT (1 μg) together with 1 μg of the empty vector, pcDNA3.1 (lane 1), or the expression vector encoding RZ-1 (lane 2) or RZ-2 (lane 3). All culture media contained $10^{-8}$ M dexamethasone. The numbers represent values minus the background activity of the negative control containing GR expression vector but not dexamethasone. The points in each histogram indicate the results from three independent transfections.

Estrogen-depleted cells were transfected with ERE-TK-Luc and cultured either in estrogen-free medium (bar 1) or in the presence of $10^{-9}$ M 17β-estradiol (bars 2–5). Histograms 1 and 2 were derived from cells transfected only with ERE-TK-Luc. Histograms 4 and 5 indicate transfections with ERE-TK-Luc plus RZ-1 and RZ-2 expression constructs, respectively. Histogram 3 indicates transfection with control vector (pcDNA3.1). Results are average of duplicate experiments, with individual values presented as dots.

Figure 6:
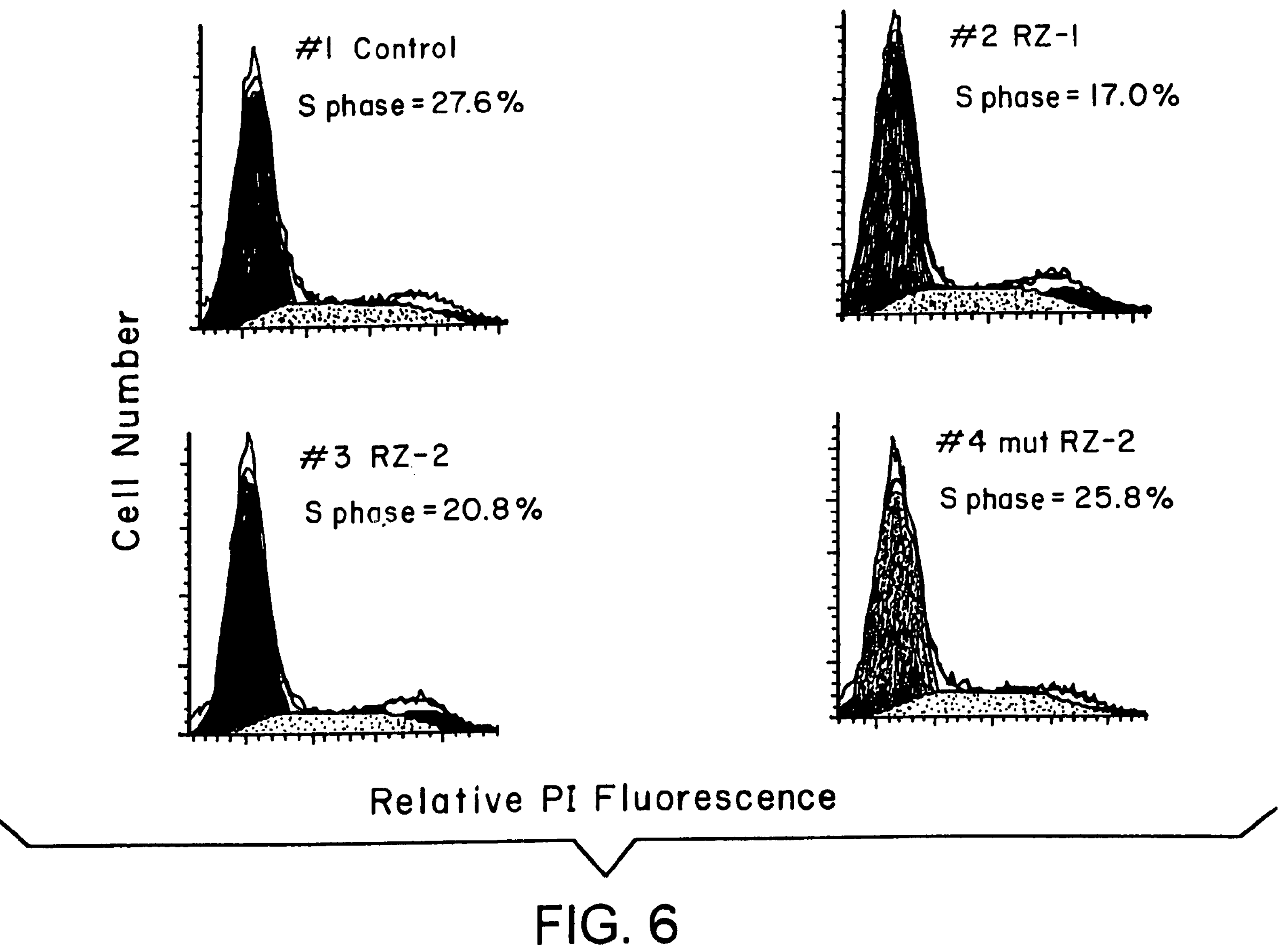

MCF-7 cells become quiescent when deprived of estrogens, but subsequent estrogen supplementation propels them into the synthetic phase of the cell cycle, leading to mitosis. Earlier studies have shown about 50% reduction of S phase cells 24 h after inhibition of estrogen action by the antiestrogenic ligand tamoxifen. Despite the limitation of transient transfections, where only a certain percentage of the cell population picks up the transfected DNA, the effects of the hERα-specific ribozymes on the percentage of S phase population was examined at 26 h after 17 β-estradiol was reintroduced into the ribozyme-expressed quiescent MCF-7 cells. The percentages of S phase populations as determined by fluorescence-activated cell sorting (FACS) are shown in FIG. 6. The results demonstrate that both RZ-1 and RZ-2 cause a reduction in the number of cells that enter into the S phase, a prelude to mitosis. All of these results taken together indicate that both RZ-1 and RZ-2 can serve as effective inhibitors of ERa expression, and they can also inhibit estrogen-dependent transcriptional activation and cell proliferation.

EXAMPLE 7

Effects of RZ-1 and RZ-2 on the Natural hERα Transcript in ER-Positive MCF-7 Cells and on the Estrogen-Dependent Cell Cycle Progression into the S Phase The inhibitory effects of the two ribozymes on promoter-reporter function in COS-1 cells transfected with the hERα expression vector indicate the efficacy of these ribozymes on the transcripts derived from processed complementary DNAs (cDNAs). To examine the ribozyme effects on the natural transcript of hERα, ER-positive MCF-7 cells were examined. MCF-7 cells are highly estrogen sensitive for ERE-TK-Luc expression without any hERα cotransfection (FIG. 5, bars 1 and 2). Cotransfection with the empty vector (pcDNA3.1) did not significantly alter luciferase activity (bar 3). However, both RZ-1 and RZ-2 caused more than 60% of inhibition of luciferase activity.

Estrogen-depleted quiescent cells were transfected with the following plasmids: poDNA3.1 empty vector (panel 1), RZ-1 (panel 2), RZ-2 (panel 3), and mutant RZ-2 (4). Transfected cells were cultured for 26 h in the presence of $10^{-9}$ M 17β-estradiol before harvesting for FACS analysis. The shaded area within the distribution profile shows S phase cell cycle populations. The FACS analysis was repeated three different times, and the figure represents the results of one of those studies. Two other studies produced similar distribution patterns, with RZ-1 causing 19% and 38% inhibition and RZ-2 causing 34% and 25% inhibition of the S phase population over the vector-treated control.

EXAMPLE 8

Recombinant Adenovirus Construction

The present example is presented to demonstrate the utility of the present invention with a variety of vectors, including a recombinant adenovirus. In order to inactivate estrogen receptor in breast tumors, an adenovirus-based system was developed and is described in the present example by the present inventors for delivery of estrogen receptor-specific ribozyme.

The use of recombinant adenoviruses in molecular biology has several advantages for exogenous gene expression. First, adenoviruses are capable of infecting a variety of cell types. Second, gene transfer is not dependent on cell division. Third, high levels of gene expression and high viral titers can be obtained. The commonly used human adenovirus serotype 5 can include transgene sequences up to 10 kb. Normal adenoviral transcripts include E1, E2, E3, and E4. E1 and E3 are commonly deleted and replaced with transgenes. Deletion of E1 renders the adenovirus defective for replication. This makes the vector incapable of producing infectious viruses in target cells. In order to generate high titers of viruses, the adenovirus must be introduced into a "packaging" cell line such as 293 or 911 cells which endogenously express E1 and allow viral production. The E3 transcript is involved in the evasion of host immune responses and is therefore not needed for viral replication (Mittal et al., 1993). The most commonly employed technique to generate the desired recombinant adenovirus is by introducing a replication-deficient adenovirus and a shuttle vector containing the transgene into a packaging cell line to allow homologous recombination. The packaging cell line provides the necessary E1 gene for generating infectious viral particles. Although this approach is useful, recombination efficiency is low and the process of screening and purifying plaques is long and tedious (Becker et al., 1994).

A novel, simplified system was used in the implementation of the present invention for generating recombinant adenoviruses, which contain estrogen receptor-specific ribozyme. Transformation of *E. coli* strain BJ5183 with adenoviral "backbone plasmid" and a shuttle vector plasmid containing the ribozyme results in homologous recombination via the bacteria's efficient recombination system (He et al., 1998). Once the desired recombinant adenovirus is identified, it can subsequently be introduced into the packaging cell line to produce infectious viral particles.

Oligodeoxynucleotides corresponding to the sequences of wild-type and mutant estrogen receptor-specific ribozymes (Lavrovsky et al., 1999) were synthesized and purified on a 16% polyacrylamide/8M urea gel. Oligodeoxynucleotides were annealed, phosphorylated and ligated into pAdtrack-CMV vector between the Xho I and Xba I sites. Generated pAdtrack-CMV-ribozyme and pAdtrack-CMV-ribozyme-mutant were linearized with PmeI, purified, mixed with supercoiled pAdEasy-1 and transformed into competent *E. coli* BJ5183 to allow homologous recombination (FIG. 8).

Clones were screened by restriction endonuclease digestion with Barn H I, EcoR I and Pac I. Sequence of recombinant adenoviral plasmids was confirmed by manual sequencing. These plasmids were transfected into 293 cells for adenovirus production.

PROPHETIC EXAMPLE 9

Gene Therapy for Breast Cancer

The present example is presented to demonstrate the utility of the present invention for the treatment of human breast cancer. Clones prepared according to that protocol provided in example 8 were screened by restriction endonuclease digestion with Bam H I, EcoR I and Pac I. Sequence of recombinant adenoviral plasmids was confirmed by manual sequencing. These plasmids were transfected into 293 cells for adenovirus production. Recombinant adenoviruses were amplified and purified as previously described (He et al., 1998).

As part of a method for treating breast cancer, the following protocol presents at least one embodiment of the proposed therapeutic method.

Each ribozyme (RZ1, RZ2, etc) will be individually cloned into adenoviral, or other viral or non-viral vector, to provide a cassette (FIG. 7). Adenoviral particles containing ribozymes as designated here RZ1 through RZ7, will be purified, mixed in equal ratio, and administered to the animal to which the treatment is to be provided. By way of example, it is envisioned that for a human, the form of the drug may be a pill, fluid, or some other form well known to those of skill in the art to be compatible for human injection. Remingtons Pharmaceutical Basis of Therapeutics may be used in the formulation of these and other embodiments of the treatment preparation, and would not involve a large amount of trial and error. Dosage amounts of the preparation will vary according to the particular mode of delivery being used, as well as the form of the active agent being used. Standard dosing protocols may be used to optimize the desired dose for a particular patient, again as well known to those of skill in the medicinal arts, and will likely vary as well during the particular stage of treatment of the patient and any other drugs or treatment regimens that the patient may be receiving.

An improvement in the patients condition, in particular a remission of the cancerous condition, would provide a benchmark of the efficacy of the particular treatment regimen of the invention being applied to the particular patient, and modified accordingly if needed.

EXAMPLE 10

The Potential Ribozyme Cleavage Sites on the ERα mRNA (Gene Bank Accession # M12674):

Positions of other GUC (GUC in RNA and GTC in corresponding cDNA) sequences are 170, 190, 267, 377, 508, 515, 543, 603, 645, 889 (cleavage site within the human mRNA for estrogen receptor for RZ-2), 894, 956 (cleavage site for RZ-1), 1137, 1218, 1240, 1420, 1463, 1468, 1680, 1695, 1726, and 2077. Sites # 889 and 956 were chosen because they met two other requirements, which are:

the site positioning in an open loop region (secondary structure) and the presence of flanking AU-rich regions.

Below is a truncated 1380 nt sequence of human ER mRNA starting from position #361 to #1740: (SEQ ID NO:4)

```
361 ggagcccctg aaccgtccgc agctcaagat ccccctggag cggcccctgg gcgaggtgta
421 cctggacagc agcaagcccg ccgtgtacaa ctaccccgag ggcgccgcct acgagttcaa
481 cgccgcggcc gccgccaacg cgcaggtcta cggtcagacc ggcctcccct acggccccgg
543 gtctgaggct gcggcgttcg gctccaacgg cctggggggt ttcccccac tcaacagcgt
603 gtctccgagc ccgctgatgc tactgcaccc gccgccgcag ctgtcgcctt tcctgcagcc
661 ccacggccag caggtgccct actacctgga gaacgagccc agcggctaca cggtgcgcga
721 ggccggcccg ccggcattct acaggccaaa ttcagataat cgacgccagg gtggcagaga
781 aagattggcc agtaccaatg acaagggaag tatggctatg gaatctgcca aggagactcg
841 ctactgtgca gtgtgcaatg actatgcttc aggctaccat tatggagtct ggtcctgtga
901 gggctgcaag gccttcttca agagaagtat tcaaggacat aacgactata tgtgtccagc
961 caccaaccag tgcaccattg ataaaaacag gaggaagagc tgccaggcct gccggctccg
```

-continued

```
1021 caaatgctac gaagtgggaa tgatgaaagg tgggatacga aaagaccgaa gaggagggag

1081 aatgttgaaa cacaagcgcc agagagatga tggggagggc aggggtgaag tggggtctgc

1141 tggagacatg agagctgcca acctttggcc aagcccgctc atgatcaaac gctctaagaa

1201 gaacagcctg gccttgtccc tgacggccga ccagatggtc agtgccttgt tggatgctga

1261 gccccccata ctctattccg agtatgatcc taccagaccc ttcagtgaag cttcgatgat

1321 gggcttactg accaacctgg cagacaggga gctggttcac atgatcaact gggcgaagag

1381 ggtgccaggc tttgtggatt tgaccctcca tgatcaggtc caccttctag aatgtgcctg

1441 gctagagatc ctgatgattg gtctcgtctg gcgctccatg gagcacccag tgaagctact

1501 gtttgctcct aacttgctct tggacaggaa ccagggaaaa tgtgtagagg gcatggtgga

1561 gatcttcgac atgctgctgg ctacatcatc tcggttccgc atgatgaatc tgcagggaga

1621 ggagtttgtg tgcctcaaat ctattatttt gcttaattct ggagtgtaca catttctgtc

1701 cagcaccctg aagtctctgg aagagaagga ccatatccac cgagtcctgg acaagatcac
```

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieve All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Mangelsdorf D K, Thummel C. Beato M, Herrlich P, Schutz G. Umesono K, Blumberg B, Kastner P, Mark M, Chambon P 19995 The nuclear receptor superfamily: the second decade. Cell 83:835–839
2. De Sombre E R, Puca G A, Jensen E V 1969 Purification of an estrophilic protein from calf uterus. Proc Natl Acad Sci USA 64:148–154
3. Kuiper G G, Enmark E. Peito-Huikko M. Nilsson S, Gustafsson J A 1996 Cloning of a novel receptor expressed in rat prostate and ovary. Proc Natl Acad Sci USA 93:5925–5930
4. Mosselman S, Polman J. Oijkema R 1996 ER beta; Identification and characterization of a novel human estrogen receptor, FEBS Lett 392:49–53
5. Hanstein B. Kiu H, Yancisin M C, Brown M 1999 Functional analysis of a novel estrogen receptor-beta isoform Mol Endocrinol 13:129–137
6. Lubahn D B, Moyer J S, Golding T S, Couse J F, Korach K S, Smithies O 1993Alteration of reproductive function but not prenatal sexual development after insertional disruption of the mouse estrogen receptor gene. Proc Natl Acad Sci USA 90:11162–11166
7. Krege J H, Hodgin J B, Couse J F, Enmark E, Warner M, Mahler J F, Sar M, Korsch K S, Gustafsson J A, Smithies O 1998 Generation and reproductive phenotypes of mice lacking estrogen receptor-β. Proc Natl Acad Sci USA 95:15877–15882
8. Jensen E V 1995 Steroid hormone antagonists, Summary and future challenges. Ann NY Acad Sci 781.1–4
9. Shieu A K, Barstad D, Loria P M, Cheng L, Kushner P J, Agard D A, Greene G L 1998 The structural basis of estrogen receptor/coactivator recognition and the antagonism of this interaction by tamoxifen. Cell 85:927–937
10. McDonnell D P, Dana S L, Hoener P A, Lieberman B A, Imhof M O, Stein R B 1995 Cellular mechanisms which distinguish between hormone- and antihormone-activated estrogen receptor. Ann NY Acad Sci 761:121–137
11. Ince B A, Schodin D J, Snapiro D J, Katzenelienbogen B S 1995 Repression of endogenous estrogen receptor activity in MCF-7 human breast cancer cells by dominate negative estrogen receptors. Endocrinology 136:3194–3199
12. Chen S. Son C S, Lavrovsky Y, Bi B. Vellanoweth R, Chatterjee B, Roy A K 1998 Catalytic cleavage of the androgen receptor messenger RNA and functional inhibition of androgen receptor activity by a hammerhead ribozyme. Mol Endocrinol 12:1558–1566
13. Kato S, Endoh H, Masuhiro Y, Kitamoto T. Uchiyama S. Sasaki H, Masushige S, Gotoh Y, Nishida E, Kawashima H, Metzger D, Chamberg 1995 Activation of the estrogen receptor through phosphorylation by mitogen-activated protein kinase. Science 270:1491–1494
14. Brooks S C, Locke E R, Soule H D 1973 Estrogen receptor in a human cell line (MCF-7) from breast carcinoma, J Biol Chem 248:6251–6253
15. Haseloff J, Goriach W L 1988 Simple RNA enzymes with new and highly specific endoribonuclease activies. Nature 334:585–591
16. Persidia A 1997 Ribozyme therapeutics, Nat Biotechnol 15:921–922
17. Hendrix C, Anne J, Joris B, Van A A, Herdawijn P 1996 Selection of hammerhead ribozymes for optimum cleavage of interieukin 6 mRNA, Biochem J 314:655–661

18. Zuker M 1909 On finding all suboptimal foldings of an RNA molecule. Science 244:48–52

19. Jarvis T C, Wincott F E, Alby L J, McSwiggen J A, Beigalman L, Gustofson J, DiRenzo A, Levy K. Arthur M, Matulic-Adamio J, Karpelsky A, Gonzalez O, Woolf T M, Usman N, Stinchcomb D T 1996 Optimizing the cell efficacy of synthetic ribozymes. Site selection and chemical modifications of ribozymes targeting the proto-oncogene c-mby, J Biol Chem 271:29107–29112

20. Hertel K J, Stage-Zummermann T K, Ammons G. Unlenbeck O C 1996 Thermodynamic dissection of the substrate-ribozyme interaction in the hammerhead ribozyme. Biochemistry 37:16983–16988

21. Trapp T., Holsboer F 1996 Nuclear ophan receptor as a repressor of glucocorticoid receptor transcriptional activity, J Biol Chem 271:29107–29112

22. Bonnelye E, Vanacker J M, Dittmar T, Begue A, Desbiens X, Dehardt D T, Aubin J E, Laudet V, Fournier B 1997 The ERR-1 orphan receptor is a transcriptional activator expressed during bone development. Mol Endoctrinol 11:905–916

23. Ernst M, Parker M G, Rodan G A 1991 Functional estrogen receptors in osteoblastic cells demonstrated by transfection with a reporter gene containing an estrogen response element. Mol Endocrinol 5:1597–1606

24. Weichselbaum R R, Hellman S, Piro A J, Nove J J, Little J B 1978 Proliferation kinetics of a human breast cancer line in vitro following treatment with 17β-estradiol and 1β-D-arabinofuranosylcytosine,m Cancer Res 38:2339–2342

25. Sutherland R L, Green M D, Hall R E, Reddel R R, Taylor I W 1983 Tamoxifen induces accumulation of MCF 7 human mammary carcinoma cells in the G0/G1 phase of the cell cycle, Eur J Cancer Olin Onool 19:615–621

26. Harper M J, Walpole A L 1967 A new derivative of triphenylethylene; effect on implantation and mode of action in rats. J Repord Fertil 13:101–119

27. Jordan Y C, Murphy C S 1990 Endocrine pharmacology of antiestrogens as antitumor agents. Endoor Rev 11:578–610

28. Grease T A, Sluka J P, Bryant H U, Cullinan G J, Glasebrook A L, Jones C D, Matsumoto K, Palkowitz A D, Sato M, Termine J K, Winter M A, Yang N N, Dodge J A 1997 Molecular determinates of tissue selectivity in estrogen receptor modulators. Proc Natl Acad Sci USA 94:14105–14110

29. Nicholson, R I, Gee J M, Manning D L, Wakeling A E, Montano M M, Katzenellenbogen B S 1995 Responsors to pure antiestrogens (ICI 164583,CIC 182780) in estrogen-sensitive and -resistant experimental and clinical breast cancer. Ann NY Acad Sci 761:148–163

30. Fuqua S A, Fitzgerald S D, Chamness G C, Tandon A K, McDonnell D P, Nawaz Z, O'Malley B W, McGuire W L 1991 Variant human breast tumor estrogen receptor with constitutive transcriptional activity. Cancer Res 51:105–109

31. Pink J J, Jiang S Y, Fritsch M,. Jordan V C 1995 An estrogen-independent MCF-7 breast cancer cell line which contains a novel β0-kilodalton estrogen receptor-related protein, Cancer Res 55:2583–2590

32. Von Angerer E, Biberger C, Leichti S 1995 Studies on heterocycle-based pure estrogen antagonists. Ann NY Acad Sci 761:176–191

33. Sachs, A B 1993 Messenger RNA degradation in eukaryotes. Cell 74:413–421

34. Burcin M M, Schiedner G, Kochanek S, Tsai S Y, O'Malley B W 1999 Adenovirus-mediated regulable target gene expression in vivo. Proc Natl Acad Sci USA 96:255–360

35. Ernst M. Parker M G, Rodan G A 1991 Functional estrogen receptors in osteoblastic cells demonstrated by transfection with a reporter gene containing an estrogen response element. Mol Endocrinol 5:1597–1606

36. Bradford M M 1976 A rapid arid sensitive method for the quantitation of microgram quantities of protein utilizing the principle of protein-dye binding. Anal Biochem 72:248–254

37. Becker, T. C., Noel, R. J., Coats, W. S., Gomez-Foix, A. M., Alam, T., Gerard, R. D., Newgard, C. B. (1994). Use of recombinant adenovirus for metabolic engineering of mammalian cells. Methods Cell Biol. 43 Pt A:161–89, 161–189.

38. He, T. C., Zhou, S., da Costa, L. T., Yu, J., Kinzler, K. W., Vogelstein, B. (1998). A simplified system for generating recombinant adenoviruses. Proc. Natl. Acad. Sci. U.S.A 95, 2509–2514.

39. Lavrovsky, Y., Tyagi, R. K., Chen, S., Song, C. S., Chatterjee, B., Roy, A. K. (1999). Ribozyme-mediated cleavage of the estrogen receptor messenger RNA and inhibition of receptor function in target cells. Mol. Endocrinol. 13, 925–934.

40. Mittal, S. K., McDermott, M. R., Johnson, D. C., Prevec, L., Graham, F. L. (1993). Monitoring foreign gene expression by a human adenovirus-based vector using the firefly luciferase gene as a reporter. Virus Res. 28, 67–90.

44. Snyder, R O (1999) Adeno-assiciated virus Mediated Gene Delivery, J. Gene Med., May-June; 1(3):166–75.

45. Sinnaeve et al (1999), Cardiovascular Research, 44:498–508.

46. Fathmar et al (2000) Clinical Immunology, 95(1): S39–S43.

47. Nettlebeck et al., (2000), TIG, 16(4):174–179.

48. Wu and Ataai, (2000), Biomedical Engineering, 11:205–208.

49. Albelda et al., (2000), Annals of Internal Medicine, 132(8):649–660.

50. Asahara et al., (2000), Gene Therapy, 7:451–457.

51. J. Andoni Urtizbea, (2000), European Neurology, 43:127–132.

52. Hajjar et al., (2000), Circ. Res. 86:616–621.

53. Buchschacher and Wong-Staal, (2000), Blood, 95(8): 2499–2504.

54. Hiltunen et al., Vas. Med. (2000), 5(1):41–8.

55. Russell and Cossett, (1999), J. Gene Med. 1(5): 300–11.

56. Remingtons Pharmaceutical Basis of Therapeutics (1992).

What is claimed is:

1. A ribozyme that cleaves estrogen receptor mRNA, wherein said ribozyme comprises the sequence of SEQ ID NO:7 (RZ1) or SEQ ID NO:11 (RZ2).

2. The ribozyme of claim 1, wherein said ribozyme comprises the sequence of SEQ ID NO:7 (RZ1).

3. The ribozyme of claim 2, wherein said ribozyme has the sequence of SEQ ID NO:7 (RZ1).

4. The ribozyme of claim 1, wherein said ribozyme comprises the sequence of SEQ ID NO: 11 (RZ2).

5. The ribozyme of claim 4, wherein said ribozyme has the sequence of SEQ ID NO:11 (RZ2).

6. The ribozyme of claim 4, wherein said ribozyme is formulated in a liposome.

7. A nucleic acid that encodes a ribozyme in accordance with claim 1.

8. The nucleic acid of claim 7, wherein said nucleic acid encodes a ribozyme that comprises the sequence of SEQ ID NO:7 (RZ1).

9. The nucleic acid of claim 7, wherein said nucleic acid encodes a ribozyme that comprises the sequence of SEQ ID NO: 11 (RZ2).

10. The nucleic acid of claim 7, wherein said nucleic acid further comprises a promoter.

11. The nucleic acid of claim 7, wherein said nucleic acid is comprised within a recombinant vector.

12. The nucleic acid of claim 11, wherein said nucleic acid is comprised within a recombinant viral vector.

13. The nucleic acid of claim 12, wherein said nucleic acid is comprised within a recombinant adenoviral vector, adeno-associated viral vector or retroviral vector.

14. An expression vector that expresses a ribozyme in accordance with claim 1.

15. The expression vector of claim 14, wherein said vector expresses a ribozyme that comprises the sequence of SEQ ID NO:7 (RZ1).

16. The expression vector of claim 14, wherein said vector expresses a ribozyme that comprises the sequence of SEQ ID NO: 11 (RZ2).

17. The expression vector of claim 14, wherein said vector provides 5' capping and polyadenylation of the expressed ribozyme.

18. A method for reducing estrogen receptor activity, comprising providing an effective amount of a ribozyme in accordance with claim 1 to estrogen receptor-containing cultured cells.

19. The method of claim 18, wherein the estrogen-dependent proliferation of said cells is inhibited.

20. A method for inhibiting estrogen-dependent cell proliferation, comprising administering a ribozyme in accordance with claim 1 to estrogen receptor-containing cells in vitro in an amount effective to inhibit proliferation of said cells.

21. The method of claim 20, wherein said ribozyme comprises the sequence of SEQ ID NO:7 (RZ1).

22. The method of claim 20, wherein said ribozyme comprises the sequence of SEQ ID NO: 11 (RZ2).

23. The method of claim 20, wherein said ribozyme is administered to said cells in a liposome.

24. The method of claim 20, wherein a vector that expresses said ribozyme is administered to said cells.

25. The method of claim 24, wherein said vector is an adenoviral vector, adeno-associated viral vector or retroviral vector.

26. The method of claim 20, wherein said estrogen receptor-containing cells are estrogen-dependent tumor cells.

27. The method of claim 26, wherein said estrogen-dependent tumor cells are estrogen-dependent breast cancer cells.

28. The method of claim 20, wherein an antiestrogen compound is further administered to said cells.

* * * * *